(12) United States Patent
Honold et al.

(10) Patent No.: US 8,067,599 B2
(45) Date of Patent: Nov. 29, 2011

(54) IMIDAZO [4,5-B] PYRIDINE AND PYRROLO [2,3-B] PYRIDINE PROTEIN KINASE INHIBITORS

(75) Inventors: Konrad Honold, Penzberg (DE); Wolfgang Schaefer, Mannheim (DE); Stefan Scheiblich, Penzberg (DE)

(73) Assignee: Hoffman-La Roche Inc., Nutley, NJ (US)

( * ) Notice: Subject to any disclaimer, the term of this patent is extended or adjusted under 35 U.S.C. 154(b) by 393 days.

(21) Appl. No.: 12/374,682

(22) PCT Filed: Sep. 4, 2007

(86) PCT No.: PCT/EP2007/007691
§ 371 (c)(1),
(2), (4) Date: Jan. 22, 2009

(87) PCT Pub. No.: WO2008/028617
PCT Pub. Date: Mar. 13, 2008

(65) Prior Publication Data
US 2009/0318428 A1    Dec. 24, 2009

(30) Foreign Application Priority Data
Sep. 6, 2006  (EP) .................................... 06018627

(51) Int. Cl.
*A61K 31/437*  (2006.01)
*C07D 471/04*  (2006.01)

(52) U.S. Cl. ......... 546/113; 546/118; 514/300; 514/303

(58) Field of Classification Search .................. 546/113, 546/118; 514/300, 303
See application file for complete search history.

(56) References Cited

FOREIGN PATENT DOCUMENTS

| WO | 2004/024897 | 3/2004 |
|---|---|---|
| WO | 2005/063746 | 7/2005 |
| WO | WO 2006/066913 | 6/2006 |
| WO | WO 2006/066914 | 6/2006 |
| WO | WO 2007/017143 | 2/2007 |
| WO | WO 2008/028617 | 3/2008 |

*Primary Examiner* — David K O Dell
(74) *Attorney, Agent, or Firm* — George W. Johnston; Patricia S. Rocha-Tramaloni; David E. Wildman

(57) ABSTRACT

Objects of the present invention are the compounds of formula I

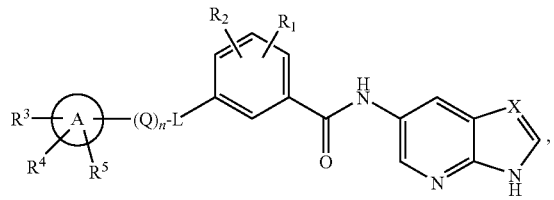

formula I their pharmaceutically acceptable salts, enantiomeric forms, diastereoisomers and racemates, the preparation of the above-mentioned compounds, medicaments containing them and their manufacture, as well as the use of the above-mentioned compounds in the control or prevention of illnesses such as cancer.

9 Claims, No Drawings

IMIDAZO [4,5-B] PYRIDINE AND PYRROLO [2,3-B] PYRIDINE PROTEIN KINASE INHIBITORS

This application claims the benefit of European Patent Application No. 06018627.7, filed Sep. 6, 2006. The entire contents of the above-identified application are hereby incorporated by reference.

The present invention relates to novel heteroaryl derivatives, to a process for their manufacture, pharmaceutical compositions containing them and their manufacture as well as the use of these compounds as pharmaceutically active agents.

BACKGROUND OF THE INVENTION

Protein kinases ("PKs") are enzymes that catalyze the phosphorylation of hydroxy groups on tyrosine, serine and threonine residues of proteins (Hunter, T., Cell 50 (1987) 823-829). The consequences of this seemingly simple activity are staggering; cell growth, differentiation and proliferation, i.e., virtually all aspects of cell life in one way or another depend on PK activity. Furthermore, abnormal PK activity has been related to a hose of disorders, ranging from relatively non-life threatening diseases such as psoriasis to extremely virulent diseases such as glioblastoma (brain cancer).

The PKs can be conveniently broken down into two classes, the protein tyrosine kinases (PTKs) and the serine-threonine kinases (STKs).

One of the prime aspects of PTK activity is their involvement with growth factor receptors. Growth factor receptors are cell surface proteins. When bound by a growth factor ligand, growth factor receptors are converted to an active form which interacts with proteins on the inner surface of a cell membrane. This leads to phosphorylation on tyrosine residues of the receptor and other proteins and to the formation inside the cell of complexes with a variety of cytoplasmic signaling molecules that, in turn, effect numerous cellular responses such as cell division (proliferation), cell differentiation, cell growth, expression of metabolic effects to the extracellular microenvironment, etc. For a more complete discussion, see Schlessinger, J., and Ullrich, A., Neuron, 9 (1992, 383-391, which is incorporated by reference, including any drawings, as if fully set forth herein.

Growth factor receptors with PTK activity are known as receptor tyrosine kinases ("RTKs"). They comprise a large family of transmembrane receptors with diverse biological activity. At present, at least nineteen (19) distinct subfamilies of RTKs have been identified. An example of these is the subfamily designated the "HER" RTKs, which include EGFR (epidermal growth factor receptor), HER2 (human epidermal growth factor receptor 2), HER3 and HER4. These RTKs consist of an extracellular glycosylated ligand binding domain, a transmembrane domain and an intracellular cytoplasmic catalytic domain that can phosphoiylate tyrosine residues on proteins.

Another RTK subfamily consists of insulin receptor (IR), insulin like growth factor I receptor (IGF-IR) and insulin receptor related receptor (IRR). IR and IGF-IR interact with insulin, IGF-I and IGF-II to form a heterotetramer of two entirely extracellular glycosylated α subunits and two β subunits which cross the cell membrane and which contain the tyrosine kinase domain.

Another RTK subfamily is referred to as the platelet derived growth factor receptor ("PDGFR") group, which includes PDGFR alpha, PDGFR beta, colony-stimulating factor I receptor (CSF-IR), c-kit and flt 3. These receptors consist of glycosylated extracellular domains composed of 5 immunoglobin-like loops and an intracellular domain wherein the tyrosine kinase domain is interrupted by a kinase inert domain.

Another group which, because of its similarity to the PDGFR subfamily, is sometimes subsumed into the latter group is the fetal liver kinase ("Flk") receptor subfamily. This group, containing extracellulos immunoglobulin loops made up of kinase insert domain-receptor fetal liver kinase-1 (KDR/Flk-1), and fins-like tyrosine kinase 1 (Flt-1 and Flt-4).

A further member of the tyrosine kinase growth factor receptor family is the fibroblast growth factor ("FGF") receptor subgroup. This group consists of four receptors, FGFR1-4, and many ligands. Although there is considerable alternative splicing, generally the receptors consist of a glycosylated extracellular domain containing 3 immunoglobin-like loops and an intracellular domain in which the tyrosine kinase sequence is interrupted by regions of a kinase insert domain.

Still another member of the tyrosine kinase growth factor receptor family is MET, often referred to as c-Met also known as human hepatocyte growth factor receptor tyrosine kinase (hHGFR). c-Met is thought to play a role in primary tumor growth and metastasis.

A more complete listing of the known RTK subfamilies is described in Plowman et al., DN&P, 7 (1994) 334-339, which is incorporated by reference, including any drawings, as if fully set forth herein.

In addition to the RTKs, there also exists a family of entirely intracellular PTKs called "non-receptor tyrosine kinases" or "cytoplasmic tyrosine kinases." This latter designation, abbreviated "CTK," will be used herein. CTKs do not contain extracellular and transmembrane domains. At present, over 24 CTKs in 11 subfamilies (Src, Frk, Btk, Csk, Abl, Zap70, Fes, Fak, Jak, LIMK and Ack) have been identified. The Src subfamily appear so far to be the largest group of CTKs and includes Src, Yes, Fyn, Lyn, Lck, Blk, Hck, Fgr, and Yrk. A further important group of CTKs is the Abl family including Abl and Arg. For a more detailed discussion of CTKs, see Bolen, J. B., Oncogene, 8 (1993) 2025-2031, which is incorporated by reference, including any drawings, as if fully set forth herein.

The serine/threonine kinases, STKs, like the CTKs, are predominantly intracellular although there are a few receptor kinases of the STK type. STKs are the most common of the cytosolic kinases; i.e. kinases that perform their function in that part of the cytoplasm other than the cytoplasmic organelles and cytoskelton. The cytosol is the region within the cell where much of the cell's intermediary metabolic and biosynthetic activity occurs; e.g., it is in the cytosol that proteins are synthesized on ribosomes. The STKs include CDk2, Raf, the ZC family of kinases, the NEK family of kinases, and BUB1.

RTKs, CTKs and STKs have all been implicated in a host of pathogenic conditions including, significantly, cancer. Other pathogenic conditions which have been associated with PTKs include, without limitation, psoriasis, hepatic cirrhosis, diabetes, angiogenesis, fibrosis, restenosis, ocular diseases, rheumatoid arthritis and other inflammatory disorders, immunological disorders such as autoimmune disease, cardiovascular disease such as atherosclerosis and a variety of renal disorders.

With regard to cancer, two of the major hypotheses advanced to explain the excessive cellular proliferation that drives tumor development relate to functions known to be PK regulated. That is, it has been suggested that malignant cell growth results from a breakdown in the mechanisms that control cell division and/or differentiation. It has been shown that the protein products of a number of proto-oncogenes are involved in the signal transduction pathways that regulate cell growth and differentiation. These protein products of proto-oncogenes include the extracellular growth factors, transmembrane growth factor PTK receptors (RTKs), cytoplasmic PTKs (CTKs) and cytosolic STKs, discussed above.

In view of the apparent link between PK-related cellular activities and wide variety of human disorders, it is no surprise that a great deal of effort is being expended in an attempt to identify ways to modulate PK activity. Some of these have been made to identify small molecules which act as PK inhibitors. WO 2006/066913 relates to imidazolopyridinyl benzamide derivatives and related compounds as src and lck kinase inhibitors.

WO 2004/024897 relate to imidazopyridines as modulators for the IgE immune response in the treatment of allergic and proliferative diseases.

SUMMARY OF THE INVENTION

The present invention relates to heteroaryl derivatives of the general formula I,

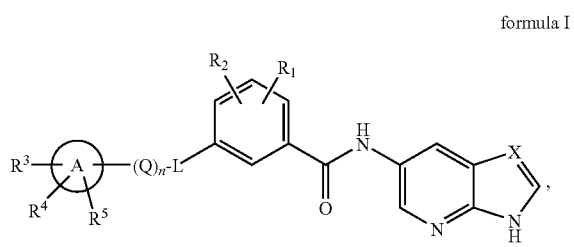

formula I wherein,
R$^1$ and R$^2$ are independently hydrogen, halogen, alkyl, alkoxy, trifluoromethyl, trifluoromethoxy, difluoromethyl or difluoromethoxy;
L is —NH—C(O)— or —C(O)—NH—;
Q is alkylene, alkenylene or cycloalkylene;
n is 0 or 1;
ring A is aryl or heteroaryl
R$^3$ is a) hydrogen or alkoxy;
  b) —V-phenyl, which is optionally substituted once or several times by fluorine, chlorine, bromine, alkyl, alkoxy, trifluoromethyl, trifluoromethoxy, cyano or —Y-alkylene-Z;
  c) heteroaryl, which is optionally substituted once or several times by fluorine, chlorine, alkyl, alkoxy, oxo, trifluoromethyl or trifluoromethoxy; or
  d) -T-heterocyclyl, which is optionally substituted once or several times by alkyl, —C(O)-alkyl, or —S(O)$_2$-alkyl;
R$^4$ is hydrogen, halogen, alkyl, alkoxy, trifluoromethyl, trifluoromethoxy, cyano or —Y-alkylene-Z;
R$^5$ is hydrogen, alkyl, fluorine, chlorine, alkoxy or cyano;
V is a single bond or —O—;
T is a single bond or alkylene;
X is N or CH;
Y is a single bond, —O—, —NR—, —S— or —S(O)$_2$;
Z is —OR, —NRR', —C(O)—NRR', cyano, —NRR'—C(O)-alkyl, —S(O)$_2$-alkyl, —S(O)$_2$NRR' or —NR—S(P)$_2$-alkyl;
R and R' are independently hydrogen or alkyl;
and all pharmaceutically acceptable salts thereof.

The compounds according to this invention show activity as protein kinase inhibitors. Many diseases are associated with abnormal cellular responses triggered by protein kinase mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

The compounds according to this invention in particular show activity as kinase inhibitors, especially as Src family kinase inhibitors (e.g. Src kinase inhibitors), Abl family kinase inhibitors (e.g. Abl kinase inhibitors), PDGFR family kinase kinase inhibitors (e.g. PDGFR beta or CSF-IR kinase inhibitors) and EGFR kinase inhibitors, and may therefore be useful for the treatment of diseases mediated by said kinases.

Src, Abl or PDGFR family kinase inhibition and EGFR inhibition exerts an antiproliferative effect in tumor cell lines. This indicates that Src, Abl or PDGFR family kinase inhibitors and EGFR kinase inhibitors may be useful in the treatment of i.e. hyperproliferative diseases such as cancer and in particular colorectal, breast, lung, prostate, pancreatic, gastric, bladder, ovarian, melanoma, neuroblastoma, cervical, kidney or renal cancers, leukemias or lymphomas.

Src family kinases are further known to be involved in a variety of other disease states. Compounds of the present invention may be further used as Src family kinase inhibitors, especially as Src kinase inhibitors, in the prevention and therapy of, for example, transplant rejection, inflammatory bowel syndrome, rheumatoid arthritis, psoriasis, restenosis, allergic asthma, Alzheimer's disease, Parkinson, stroke, osteoporosis and benign.

Abl family kinases are further known to be involved in a variety of other disease states. Compounds of the present invention may be further used as Abl family kinase inhibitors, especially as Abl kinase inhibitors, in the prevention and therapy of, for example, neurodegenerative disease, rheumatoid arthritis and diabetes, including type I or type II diabetes.

PDGFR family kinases are further known to be involved in a variety of other disease states. Compounds of the present, invention may be further used as PDGFR family kinase inhibitors, especially as PDGFR kinase inhibitors, in the prevention and therapy of, for example, diabetes, including type I or type II diabetes, restenosis (e.g. balloon injury induced restenosis), atherosclerosis or pulmonary fibrosis.

Objects of the present invention are the compounds of formula I and their tautomers, pharmaceutically acceptable salts, enantiomeric forms, diastereoisomers and racemates, their use as protein kinase inhibitors, in particular as Src, Abl or PDGFR family kinase inhibitors and EGFR kinase inhibitors, the preparation of the above mentioned compounds, medicaments or pharmaceutical compositions containing them and their manufacture as well as the use of the above-mentioned compounds in treatment, control or prevention of illnesses, especially of illnesses and disorders as mentioned above like tumors or cancer (e.g. colorectal, breast, lung, prostate, pancreatic, gastric, bladder, ovarian, melanoma, neuroblastoma, cervical, kidney or renal cancers, leukemias or lymphomas) or in the manufacture of corresponding medicaments or pharmaceutical compositions.

DETAILED DESCRIPTION OF THE INVENTION

1. Definitions

The term "alkyl" as used herein means a saturated, straight-chain or branched-chain hydrocarbon containing from 1 to 6 carbon atoms, preferably from 1 to 4 carbon atoms, such as methyl, ethyl, n-propyl, isopropyl, n-butyl, 2-butyl, t-butyl, n-pentyl, n-hexyl, preferably methyl, ethyl, isopropyl or t-butyl.

The term "alkoxy" as used herein means an alkyl O group wherein the alkyl is defined as above, preferably methoxy.

The term "halogen" as used herein means fluorine, chlorine, bromine or iodine, preferably fluorine, chlorine or bromine more preferably fluorine or chlorine.

The term "aryl" as used herein means a mono- or bicyclic aromatic ring with 6 to 10 ring carbon atoms. Examples of such aryl groups are phenyl and naphthyl, preferably phenyl.

The term "heteroaryl" as used herein means a mono- or bicyclic fully or partly unsaturated ring system with 5 to 10 ring atoms, preferably with 5 to 6 ring atoms, which contains up to 3 heteroatoms, preferably 1 or 2 heteroatoms, selected independently from N, O or S and the remaining ring atoms being carbon atoms. Preferably the heteroaryl group is fully unsaturated i.e. In one embodiment of the invention the heteroaryl group is fully unsaturated and L is —C(O)—NH—. In another embodiment of the invention the heteroaryl group is either fully or partly unsaturated and L is, —NH—C(O)—.

Examples of such fully unsaturated heteroaryl groups include pyrrolyl, imidazolyl, pyrazolyl, triazolyl, tetrazolyl, furanyl, oxazolyl, isoxazolyl, thienyl, thiazolyl, pyridyl, pyrimidyl, pyridazinyl, pyrazinyl, indolyl, indazolyl, benzimidazolyl, benzothiophenyl, benzofuranyl, quinolyl, isoquinolyl, quinazolinyl, quinoxalinyl and the like, preferably pyrazolyl, isoxazolyl, oxazolyl, quinolyl, pyridyl, pyridazinyl or pyrimidyl.

Examples of such partly unsaturated heteroaryl groups include 5,6,7,8-tetrahydro-quinazolin-2-yl, 2,3-dihydro-1H-indol-5-yl, 2,3-dihydro-1H-indol-6-yl, 3,4-dihydro-2H-benzo[1,4]thiazin-7-yl, 1,2,3,4-tetrahydro-quinoline-6-yl, 1,2,3,4-tetrahydro-quinoline-7-yl, 3-oxo-3,4-dihydro-2H-benzo[1,4]oxazin-6-yl, 3,4-dihydro-2H-benzo[1,4]oxazin-7-yl, and the like, preferably 3-oxo-3,4-dihydro-2H-benzo[1,4]oxazin-6-yl, 3,4-dihydro-2H-benzo[1,4]oxazin-7-yl, 5,6,7,8-tetrahydro-quinazolin-2-yl, 2,3-dihydro-1H-indol-5-yl or 3,4-dihydro-2H-benzo[1,4]thiazin-7-yl.

Preferably the heteroaryl of ring A is selected from pyrazolyl, isoxazolyl, quinolyl, pyridyl, pyridazinyl, pyrimidyl, 3-oxo-3,4-dihydro-2H-benzo[1,4]oxazin-6-yl, 3,4-dihydro-2H-benzo[1,4]oxazin-7-yl, 5,6,7,8-tetrahydro-quinazolin-2-yl, 2,3-dihydro-1H-indol-5-yl or 3,4-dihydro-2H-benzo[1,4]thiazin-7-yl.

Preferably the heteroaryl of $R^3$ is selected from pyrazolyl or oxazolyl.

The term "heterocyclyl" as used herein means a saturated, monocyclic ring with 5 to 6 ring atoms which contains up to 3 heteroatoms, preferably 1 or 2 heteroatoms, selected independently from N, O or S and the remaining ring atoms being carbon atoms. Preferably at least one heteroatom of the ring is N and the remaining heteroatoms are selected independently from N, O or S and such heterocyclyl group is preferably attached via the ring N atom. Examples of such saturated heterocyclic groups pyrrolidinyl, morpholinyl, piperazinyl, piperidyl, oxazolidinyl, thiazolidinyl, and the like, preferably morpholinyl or piperazinyl, and more preferably morpholinyl.

The term "alkylene" as used herein means a saturated, straight-chain or branched-chain, preferably straight-chain, hydrocarbon containing from 1 to 5 carbon atoms, preferably from 1 to 3 carbon atoms, such as methylene, ethylene, trimethylene (1,3-propylene); tetramethylene (butylene), pentamethylene, methyl-methylene, dimethyl-methylene, ethyl methylene, methyl-ethylene (1,2-propylene), ethyl-ethylene, propyl-ethylene, 1-methyl-trimethylene, 2-methyl-trimethylene, 1-ethyl-trimethylene, 2-ethyl-trimethylene and the like, preferably methylene, ethylene, trimethylene, dimethyl-methylene or methyl-methylene.

The term "alkenylene" as used herein means an unsaturated, straight-chain or branched-chain, preferably straight-chain hydrocarbon containing one double bond and containing from 2 to 5 carbon atoms, preferably from 2 to 3 carbon atoms. Examples of such "alkenylenes" are vinylene (ethenylene), methyl-vinylenel-propenylene, 2-methyl-1-propenylene, 1-butenylene, 2-butenylene, 3-butenylene, 2-ethyl-1-butenylene, 2-pentenylene, 3-pentenylene, 4-pentenylene, 4-methyl-3-pentenylene and the like, preferably vinylene or methyl-vinylene and more preferably vinylene.

The term "cycloalkylene" as used herein means a monocyclic saturated hydrocarbon ring with 3 to 6 ring atoms, preferably with 3 to 5 ring atoms. Examples of such cycloalkylene groups are 1,2-cyclopropylene, 1,1-cyclopropylene, 1,3-cyclobutylene, 1,3-cyclopentylene and the like, preferably 1,2-cyclopropylene or 1,1-cyclopropylene and more preferably 1,2-cyclopropylene.

As used herein, a "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

As used herein, the term "a therapeutically effective amount" of a compound means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

2. Detailed Description $R^1$ and $R^2$ are independently from each other, hydrogen, halogen, alkyl, alkoxy, trifluoromethyl, trifluoromethoxy, difluoromethyl or difluoromethoxy, preferably hydrogen, fluorine, chlorine, bromine, alkyl, alkoxy, trifluoromethyl or trifluoromethoxy, more preferably hydrogen, chlorine, fluorine or methyl and still more preferably hydrogen, chlorine or methyl. Preferably only one of $R^1$ and $R^2$ is hydrogen.

L is —NH—C(O) or —C(O)—NH—.

Q is alkylene, alkenylene or cycloalkylene, preferably alkenylene or cycloalkylene, and more preferably alkenylene.

n is 0 or 1, preferably 0.

ring A is aryl or heteroaryl, preferably phenyl or a heteroaryl selected from the group consisting of pyrazolyl, isoxazolyl, quinolyl, pyridyl, pyridazinyl, pyrimidyl, 3-oxo-3,4-dihydro-2H-benzo[1,4]oxazin-6-yl, 3,4-dihydro-2H-benzo[1,4]oxazin-7-yl, 5,6,7,8-tetrahydro-quinazolin-2-yl, 2,3-dihydro-1H-indol-5-yl or 3,4-dihydro-2H-benzo[1,4]thiazin-7-yl.

$R^3$ is a) hydrogen or alkoxy, preferably hydrogen;
b) —V-phenyl, which is optionally substituted once or several times, preferably once or twice, by fluorine, chlorine, bromine, alkyl, alkoxy, trifluoromethyl, trifluoromethoxy, cyano or —Y-alkylene-Z, preferably by chlorine or —Y-alkylene-Z,
c) heteroaryl, which is optionally substituted once or several times, preferably once or twice, by fluorine, chlorine, alkyl, alkoxy, oxo, trifluoromethyl or trifluoromethoxy, preferably by alkyl; or
d) -T-heterocyclyl, which is optionally substituted once or several times, preferably once or twice, by alkyl, —C(O)-alkyl or S(O)$_2$-alkyl, preferably by alkyl.

$R^4$ is hydrogen, halogen, alkyl, alkoxy, trifluoromethyl, trifluoromethoxy, cyano or —Y-alkylene-Z, preferably hydrogen, chlorine or alkoxy.
$R^5$ is hydrogen, alkyl, fluorine, chlorine, alkoxy or cyano; preferably hydrogen.
V is a single bond or —O—; preferably a single bond.
T is a single bond or alkylene, preferably a single bond.
X is N or CH, preferably CH.
Y is a single bond, —O—, —NR—, —S— or —S(O)$_2$—, preferably a single bond, —O—, —NR— or —S—, and more preferably a single bond, —O— or —S—;
Z is —OR, —NRR', —C(O)—NRR', cyano, —NRR'—C(O)-alkyl, —S(O)$_2$-alkyl, —S(O)$_2$—NRR' or —NR—S(O)$_2$-alkyl, preferably —OR, —NRR' or —C(O)—NRR' or cyano and more preferably —NRR', —C(O)—NRR' or cyano.
R and R' are independently from each other, hydrogen or alkyl.

An embodiment of the invention are the compounds according to formula I, wherein
$R^3$ is a) hydrogen;
b) —V-phenyl, which is optionally substituted once or several times by fluorine, chlorine, bromine, alkyl, alkoxy, trifluoromethyl, trifluoromethoxy, cyano or —Y-alkylene-Z;
c) heteroaryl, which is optionally substituted once or several times by fluorine, chlorine, alkyl, alkoxy, oxo, trifluoromethyl or trifluoromethoxy; or
d) -T-heterocyclyl, which is optionally substituted once or several times by alkyl, —C(O)-alkyl, or —S(O)$_2$-alkyl; and
$R^5$ is hydrogen, fluorine, chlorine, alkoxy or cyano.

Another embodiment of the invention are the compounds according to formula I, wherein
$R^1$ and $R^2$ are independently hydrogen, chlorine, fluorine or methyl;
Q is alkenylene or cycloalkylene;
n is 0 or 1;
ring A is phenyl or a heteroaryl selected from the group consisting of pyrazolyl, isoxazolyl, quinolyl, pyridyl, pyridazinyl, pyrimidyl, 3-oxo-3,4-dihydro-2H-benzo[1,4]oxazin-6-yl, 3,4-dihydro-2H-benzo[1,4]oxazin-7-yl, 5,6,7,8-tetrahydroquinazolin-2-yl, 2,3-dihydro-1H-indol-5-yl or 3,4-dihydro-2H-benzo[1,4]thiazin-7-yl;
$R^3$ is a) hydrogen or alkoxy;
b) —V-phenyl, which is optionally substituted once or twice by chlorine, alkoxy, or —Y-alkylene-Z;
c) heteroaryl is selected from pyrazolyl or oxazolyl, which is optionally substituted once or twice by alkyl; or
d) -T-morpholinyl;
$R^4$ is hydrogen, chlorine, alkyl, alkoxy, trifluoromethyl, trifluoromethoxy or —Y-alkylene-Z;
$R^5$ is hydrogen, alkyl, fluorine, chlorine, alkoxy or cyano;
T is a single bond;
X is N or CH;
Y is a single bond, —O—, —NR— or —S—;
Z is —OR, —NRR', —C(O)NRR', cyano; and
R and R' are independently hydrogen or alkyl;

Such compounds, for example, may be selected from the group consist mg of:
2-Chloro-5-(3-chloro-4-fluoro-benzoylamino)N-(1H-pyrrolo[2,3-b]pyridin-5-yl)-benzamide;
1-(2-Methoxy-phenyl)-1H-pyrazole-3-carboxylic acid[4-chloro-3-(1H-pyrrolo[2,3-b]pyridin-5-ylcarbamoyl)-phenyl]-amide;
3,4,5-Trimethoxy-N-[4-methyl-3-(1H-pyrrolo[2,3-b]pyridin-5-ylcarbamoyl)-phenyl]-benzamide;
2,4,5-Trimethoxy-N-[4-methyl-3-(1H-pyrrolo[2,3-b]pyridin-5-ylcarbamoyl)-phenyl]-benzamide;
1-Phenyl-1H-pyrazole-4-carboxylic acid[4-methyl-3-(1H-pyrrolo[2,3-b]pyridin-5-ylcarbamoyl)-phenyl]-amide;
2-Methyl-5-(2-fluoro-5-trifluoromethyl-benzoylamino)-N-(1H-pyrrolo[2,3-b]pyridin-5-yl)-benzamide;
5-tert-Butyl-2-methyl-2H-pyrazole-3-carboxylic acid[4-methyl-3-(1H-pyrrolo[2,3-b]pyridin-5-ylcarbamoyl)phenyl] amide;
2-Methyl-5-(3-morpholin-4-yl-benzoylamino)-N-(1H-pyrrolo[2,3-b]pyridin-5-yl)-benzamide;
5-[(E)-3-(2-Methoxy-phenyl)-acryloylamino]-2-methyl-N-(1H-pyrrolo[2,3-b]pyridin-5-yl)-benzamide;
5-[(E)-3-(2,4-Dimethoxy-phenyl)-acryloylamino]-2-methyl-N-(1H-pyrrolo[2,3-b]pyridin-5-yl)-benzamide;
4-Methoxy-quinoline-2-carboxylic acid[4-methyl-3-(1H-pyrrolo[2,3-b]pyridin-5-ylcarbamoyl)-phenyl]-amide;
2-Methyl-5-(2-methoxy-5-trifluoromethoxy-benzoylamino)-N-(1H-pyrrolo[2,3-b]pyridin-5-yl)-benzamide;
3-(2-Chloro-phenyl)-isoxazole-5-carboxylic acid[4-methyl-3-(1H-pyrrolo[2,3-b]pyridin-5-ylcarbamoyl)-phenyl]-amide;
5-[(Z)-3-(2-Methoxy-phenyl)-acryloylamino]-2-methyl-N-(1H-pyrrolo[2,3-b]pyridin-5-yl)-benzamide;
2-Chloro-4-fluoro-5-(2-methoxy-5-trifluoromethoxy-benzoylamino)-N-(1H-pyrrolo[2,3-b]pyridin-5-yl)-benzamide;
1-Phenyl-1H-pyrazole-3-carboxylic acid[4-chloro-2-fluoro-5-(1H-pyrrolo[2,3-b]pyridin-5-ylcarbamoyl)-phenyl]-amide;
4 Methoxy-quinoline-2-carboxylic acid[4-chloro-2-fluoro-5-(1H-pyrrolo[2,3-b]pyridin-5-ylcarbamoyl)-phenyl]-amide;
5-tert-Butyl-2-methyl-2H-pyrazole-3-carboxylic acid[4-chloro-2-fluoro-5-(1H-pyrrolo[2,3-b]pyridin-5-ylcarbamoyl)-phenyl]-amide;
2-Chloro-4-fluoro-5-(3-morpholin-4-yl-benzoylamino)-N-(1H-pyrrolo[2,3-b]pyridin-5-yl)-benzamide;
2-Chloro-4-fluoro-5-(2-fluoro-4-trifluoromethyl-benzoylamino)-N-(1H-pyrrolo[2,3-b]pyridin-5-yl)-benzamide;
2-Chloro-4-fluoro-5-(2,4,5-trimethoxy-benzoylamino)-N-(1H-pyrrolo[2,3-b]pyridin-5-yl)-benzamide;
2-Chloro-4-fluoro-5-[(E)-3-(2-methoxy-phenyl)-acryloylamino]-N-(1H-pyrrolo[2,3-b]pyridin-5-yl)-benzamide;
2-Chloro-4-fluoro-5-(3,4,5-trimethoxy-benzoylamino)-N-(1H-pyrrolo[2,3-b]pyridin-5-yl)-benzamide;

3-(2-Chloro-phenyl)isoxazole-5-carboxylic acid[4-chloro-2-fluoro-5-(1H-pyrrolo[2,3-b]pyridin-5-ylcarbamoyl)-phenyl]-amide;
4-Methyl-$N^3$-(1H-pyrrolo[2,3-b]pyridin-5-yl)-$N^1$-(6-trifluoromethyl-pyridin-3-yl)-isophthalamide;
$N^1$-(2-Methoxy-5-trifluoromethyl-phenyl)-4-methyl-$N^3$-(1H-pyrrolo[2,3-b]pyridin-5-yl)-isophthalamide;
4-Methyl-$N^1$-(2-phenyl-cyclopropyl)-$N^3$-(1H-pyrrolo[2,3-b]pyridin-5-yl)-isophthalamide;
4-Methyl-$N^1$-(3-oxazol-5-yl-phenyl)-$N^3$-(1H-pyrrolo[2,3-b]pyridin-5-yl)-isophthalamide;
$N^1$-(3-Methoxy-5-trifluoromethyl-phenyl)-4-methyl-$N^3$-(1H-pyrrolo[2,3-b]pyridin-5-yl)-isophthalamide;
4-Methyl-$N^3$-(1H-pyrrolo[2,3-b]pyridin-5-yl)-$N^1$-(3,4,5-trimethoxy-phenyl)-isophthalamide;
$N^1$-(5-tert-Butyl-2-methyl-2H-pyrazol-3-yl)-4-methyl-$N^3$-(1H-pyrrolo[2,3-b]pyridin-5-yl)-isophthalamide;
4-Methyl-$N^1$-(3-morpholin-4-yl-phenyl)-$N^3$-(1H-pyrrolo[2,3-b]pyridin-5-yl)-isophthalamide;
4-Methyl-$N^1$-(3-pyrazol-1-yl-phenyl)-$N^3$-(1H-pyrrolo[2,3-b]pyridin-5-yl)-isophthalamide; and
2-Chloro-5-[4-(2-hydroxyethyl)amino-3-chloro-benzoylamino]-N-(1H-pyrrolo[2,3-b]pyridin-5-yl)-benzamide.

Another embodiment of the invention are the compounds according to formula I, wherein
$R^1$ is chlorine or alkyl;
$R^2$ is hydrogen;
L is —C(O)—NH—;
Q is alkenylene or cycloalkylene;
n is 0 or 1;
$R^3$ is a) hydrogen;
  b) —V-phenyl, which is optionally substituted once or several times by chlorine or —Y-alkylene-Z;
  c) heteroaryl; or
  d) -T-heterocyclyl;
$R^4$ is hydrogen, halogen, alkyl, alkoxy, —Y-alkylene-Z;
$R^5$ is hydrogen;
T is a single bond;
X is CH or N, preferably CH;
Y is a single bond, —O— or —S—;
Z is —NRR', —C(O)—NRR' or cyano; and
R and R' are independently hydrogen or alkyl.

An embodiment of the invention are the compounds according to formula I, wherein
L is —C(O)—NH—.

Another embodiment of the invention are the compounds according to formula I, wherein
$R^1$ and $R^2$ are independently hydrogen, chlorine or alkyl;
L is —C(O)—NH—;
Q is alkenylene or cycloalkylene, preferably alkenylene;
n is 0 or 1;
$R^3$ is a) hydrogen;
  b) —V-phenyl, which is optionally substituted once or several times by chlorine or —Y-alkylene-Z;
  c) heteroaryl; or
  d) -T-heterocyclyl;
$R^4$ is hydrogen, halogen, alkyl, alkoxy, —Y-alkylene-Z;
$R^5$ is hydrogen;
V is a single bond;
T is a single bond;
Y is a single bond, —O— or —S—;
Z is —NRR', —C(O)—NRR' or cyano; and
R and R' are independently hydrogen or alkyl.

Another embodiment of the invention are the compounds according to formula I, wherein
X is CH.

Another embodiment of the invention are the compounds according to formula I, wherein
n is 0; and
ring A is aryl.

Another embodiment of the invention are the compounds according to formula I, wherein
$R^1$ and $R^2$ are independently hydrogen, chlorine or alkyl;
L is —C(O)—NH—;
Q is alkenylene or cycloalkylene, preferably alkenylene;
n is 0;
ring A is aryl;
$R^3$ is a) hydrogen;
  b) —V-phenyl, which is optionally substituted once or several times by chlorine or —Y-alkylene-Z;
  c) heteroaryl; or
  d) -T-heterocyclyl;
$R^4$ is hydrogen, halogen, alkyl, alkoxy, —Y-alkylene Z;
$R^5$ is hydrogen;
V is a single bond;
T is a single bond;
X is CH;
Y is a single bond, —O— or —S—;
Z is —NRR', —C(O)—NRR' or cyano; and
R and R' are independently hydrogen or alkyl.

Such compounds, for example, may be selected from the group consisting of:
3'-(2-Dimethylamino-ethoxy)-biphenyl-4-carboxylic acid [4-chloro-3-(1H-pyrrolo[2,3-b]pyridin-5-ylcarbamoyl)-phenyl]-amide;
3'-(1-Carbamoyl-ethylsulfanyl)-biphenyl-4-carboxylic acid [4-chloro-3-(1H-pyrrolo[2,3-b]pyridin-5-ylcarbamoyl)-phenyl]-amide;
Biphenyl-3-carboxylic acid[4-chloro-3-(1H-pyrrolo[2,3-b]pyridin-5-ylcarbamoyl)phenyl]-amide;
Biphenyl-4-carboxylic acid[4-chloro-3-(1H-pyrrolo[2,3-b]pyridin-5-ylcarbamoyl)-phenyl]-amide;
2-Chloro-5-(4-morpholin-4-yl-benzoylamino)-N-(1H-pyrrolo[2,3-b]pyridin-5-yl)-benzamide;
2-Chloro-5-[(3,5-dimethyl-1H-pyrazol-4-yl)-benzoylamino]-N-(1H-pyrrolo[2,3-b]pyridin-5-yl)-benzamide;
2-Chloro-5-(3-morpholin-4-yl-benzoylamino)-N-(1H-pyrrolo[2,3-b]pyridin-5-yl)-benzamide;
5-(4-tert-Butoxy-benzoylamino)-2-chloro-N-(1H-pyrrolo[2,3-b]pyridin-5-yl)-benzamide; and
2-Chloro-5-[3-(cyano-dimethyl-methyl)-benzoylamino]-N-(1H-pyrrolo[2,3-b]pyridin-5-yl)benzamide.

Another embodiment of the invention are the compounds according to formula I, wherein
n is 0; and
ring A is heteroaryl.

Another embodiment of the invention are the compounds according to formula I, wherein
$R^1$ and $R^2$ are independently hydrogen, chlorine or alkyl;
L is —C(O)—NH—;
Q is alkenylene or cycloalkylene, preferably alkenylene;
n is 0;
ring A is heteroaryl;
$R^3$ is a) hydrogen;
  b) —V-phenyl, which is optionally substituted once or several times by chlorine or —Y-alkylene-Z;
  c) heteroaryl; or
  d) -T-heterocyclyl;
$R^4$ is hydrogen, halogen, alkyl, alkoxy, —Y-alkylene-Z;
$R^5$ is hydrogen;
V is a single bond;
T is a single bond;
X is CH;

Y is a single bond, —O— or —S—;
Z is —NRR', —C(O)—NRR' or cyano; and
R and R' are independently hydrogen or alkyl.
Such compounds, for example, may be selected from the group consisting of:
3-(2-Chloro-phenyl)-isoxazole-5-carboxylic acid[4-chloro-3-(1H-pyrrolo[2,3-b]pyridin-5-ylcarbamoyl)-phenyl]-amide; and
5-Methyl-1-phenyl-1H-pyrazole-4-carboxylic acid[4-chloro-3-(1H-pyrrolo[2,3-b]pyridin-5-ylcarbamoyl)-phenyl]-amide.

Another embodiment of the invention are the compounds according to formula I, wherein
n is 1; and
ring A is aryl.

Another embodiment of the invention are the compounds according to formula I, wherein
$R^1$ and $R^2$ are independently hydrogen, chlorine or alkyl;
L is —C(O)—NH—;
Q is alkenylene or cycloalkylene, preferably alkenylene;
n is 1;
ring A is aryl;
$R^3$ is a) hydrogen;
  b) —V-phenyl, which is optionally substituted once or several times by chlorine or —Y-alkylene-Z;
  c) heteroaryl; or
  d) -T-heterocyclyl;
$R^4$ is hydrogen, halogen, alkyl, alkoxy, —Y-alkylene-Z;
$R^5$ is hydrogen;
V is a single bond;
T is a single bond;
X is CH;
Y is a single bond, —O— or —S—;
Z is —NRR', —C(O)—NRR' or cyano; and
R and R' are independently hydrogen or alkyl.
Such compounds, for example, may be selected from the group consisting of:
2-Chloro-5-((E)-3-phenyl-but-2-enoylamino)-N-(1H-pyrrolo[2,3-b]pyridin-5-yl)-benzamide;
2-Chloro-5-[3-[4-(3-dimethylamino-propoxy)-phenyl]-acryloylamino]-N-(1H-pyrrolo[2,3-b]pyridin-5-yl)-benzamide;
2-Chloro-5-[3-(3-cyano-phenyl)-2-methyl-acryloylamino]-N-(1H-pyrrolo[2,3-b]pyridin-5-yl)-benzamide;
2-Chloro-5-[(E)-3-(2-methoxy-phenyl)-acryloylamino]-N-(1H-pyrrolo[2,3-b]pyridin-5-yl)-benzamide; and
2-Chloro-5-{[(1S,2S)-2-(4-methoxy-phenyl)-cyclopropanecarbonyl]-amino}-N-(1H-pyrrolo[2,3-b]pyridin-5-yl)-benzamide.

Another embodiment of the invention are the compounds according to formula I, wherein
n is 1; and
ring A is heteroaryl.

Another embodiment of the invention are the compounds according to formula I, wherein
$R^1$ and $R^2$ are independently hydrogen, chlorine or alkyl;
L is —C(O)—NH—;
Q is alkenylene or cycloalkylene, preferably alkenylene;
n is 1;
ring A is heteroaryl;
$R^3$ is a) hydrogen;
  b) —V-phenyl, which is optionally substituted once or several times by chlorine or —Y-alkylene-Z;
  c) heteroaryl; or
  d) -T-heterocyclyl;
$R^4$ is hydrogen, halogen, alkyl, alkoxy, —Y-alkylene-Z;
$R^5$ is hydrogen;
V is a single bond;
T is a single bond;
X is CH;
Y is a single bond, —O— or —S—;
Z is NRR', —C(O)—NRR' or cyano; and
R and R' are independently hydrogen or alkyl.
Such compounds, for example, may be selected from the group consisting of:
2-Chloro-5-((E)-3-pyrimidin-5-yl-acryloylamino)-N-(1H-pyrrolo[2,3-b]pyridin-5-yl)-benzamide; and
2-Chloro-5-((E)-3-pyridazin-3-yl-acryloylamino)-N-(1H-pyrrolo[2,3-b]pyridin-5-yl)-benzamide.

Another embodiment of the invention are the compounds according to formula I, wherein
X is N.

Another embodiment of the invention are the compounds according to formula I, wherein
n is 0; and
ring A is aryl.

Another embodiment of the invention are the compounds according to formula I, wherein
$R^1$ and $R^2$ are independently hydrogen, chlorine or alkyl;
L is —C(O)NH—;
Q is alkenylene or cycloalkylene, preferably alkenylene;
n is 0;
ring A is aryl;
$R^3$ is a) hydrogen;
  b) —V-phenyl, which is optionally substituted once or several times by chlorine or —Y-alkylene-Z;
  c) heteroaryl; or
  d) -T-heterocyclyl;
$R^4$ is hydrogen, halogen, alkyl, alkoxy, —Y-alkylene-Z;
$R^5$ is hydrogen;
V is a single bond;
T is a single bond;
X is N;
Y is a single bond, —O— or —S—;
Z is —NRR', —C(O)—NRR' or cyano; and
R and R' are independently hydrogen or alkyl.
Such compounds, for example, may be selected from the group consisting of:
5-Benzoylamino-N-(3H-imidazo[4,5-b]pyridin-6-yl)-2-methyl-benzamide;
Biphenyl-3-carboxylic acid[3-(3H-imidazo[4,5-b]pyridin-6-ylcarbamoyl)-4-methyl-phenyl]-amide; and
Biphenyl-4-carboxylic acid[3-(3H-imidazo[4,5-b]pyridin-6-ylcarbamoyl)-4-methyl-phenyl]-amide.

Another embodiment of the invention are the compounds according to formula I, wherein
n is 0; and
ring A is heteroaryl.

Another embodiment of the invention are the compounds according to formula I, wherein
$R^1$ and $R^2$ are independently hydrogen, chlorine or alkyl;
L is —C(O)—NH—;
Q is alkenylene or cycloalkylene, preferably alkenylene;
n is 0;
ring A is heteroaryl;
$R^3$ is a) hydrogen;
  b) —V-phenyl, which is optionally substituted once or several times by chlorine or —Y-alkylene-Z;
  c) heteroaryl; or
  d) -T-heterocyclyl;
$R^4$ is hydrogen, halogen, alkyl, alkoxy, —Y-alkylene-Z;
$R^5$ is hydrogen;
V is a single bond;
T is a single bond;

X is N;
Y is a single bond, —O— or —S—;
Z is —NRR', —C(O)—NRR' or cyano; and
R and R' are independently hydrogen or alkyl.

Another embodiment of the invention are the compounds according to formula I, wherein
n is 1; and
ring A is aryl.

Another embodiment of the invention are the compounds according to formula I, wherein
$R^1$ and $R^2$ are independently hydrogen, chlorine or alkyl;
L is —C(O)—NH—;
Q is alkenylene or cycloalkylene, preferably alkenylene;
n is 1;
ring A is aryl;
$R^3$ is a) hydrogen;
  b) —V-phenyl, which is optionally substituted once or several times by chlorine or —Y-alkylene-Z;
  c) heteroaryl; or
  d) -T-heterocyclyl;
$R^4$ is hydrogen, halogen, alkyl, alkoxy, —Y-alkylene-Z;
$R^5$ is hydrogen;
V is a single bond;
T is a single bond;
X is N;
Y is a single bond, —O— or —S—;
Z is —NRR', —C(O)—NRR' or cyano; and
R and R' are independently hydrogen or alkyl.

Such a compound is for example:
N-(3H-Imidazo[4,5-b]pyridin-6-yl)-2-methyl-5-[(E)-(3-phenyl-acryloyl)amino]-benzamide.

Another embodiment of the invention are the compounds according to formula I, wherein
n is 1; and
ring A is heteroaryl.

Another embodiment of the invention are the compounds according to formula I, wherein
$R^1$ and $R^2$ are independently hydrogen, chlorine or alkyl;
L is —C(O)—NH—;
Q is alkenylene or cycloalkylene, preferably alkenylene;
n is 1;
ring A is heteroaryl;
$R^3$ is a) hydrogen;
  b) —V-phenyl, which is optionally substituted once or several times by chlorine or —Y-alkylene-Z;
  c) heteroaryl; or
  d) -T-heterocyclyl;
$R^4$ is hydrogen, halogen, alkyl, alkoxy, —Y-alkylene-Z;
$R^5$ is hydrogen;
Y is a single bond;
T is a single bond;
X is N;
Y is a single bond, —O— or —S—;
Z is —NRR', —C(O)—NRR' or cyano; and
R and R' are independently hydrogen or alkyl.

Another embodiment of the invention are the compounds according to formula I, wherein
L is —NH—C(O)—.

Another embodiment of the invention are the compounds according to formula I, wherein
$R^1$ and $R^2$ are independently chlorine or alkyl;
L is —NH—C(O)—;
Q is alkylene or cycloalkylene, preferably cycloalkylene;
n is 0 or 1, preferably 0;
$R^3$ is a) hydrogen;
  b) —V-phenyl, which is optionally substituted once or several times by chlorine or —Y-alkylene-Z;
  c) heteroaryl; or
  d) -T-heterocyclyl;
$R^4$ is hydrogen, halogen, alkyl, alkoxy, —Y-alkylene-Z;
$R^5$ is hydrogen;
T is a single bond;
Y is a single bond, —O— or —S—;
Z is —NRR', —C(O)—NRR' or cyano; and
R and R' are independently hydrogen or alkyl.

Another embodiment of the invention are the compounds according to formula I, wherein
$R^1$ and $R^2$ are independently chlorine or alkyl;
L is —NH—C(O)—;
Q is alkylene or cycloalkylene, preferably cycloalkylene;
n is 0;
ring A is aryl;
$R^3$ is a) hydrogen;
  b) —V-phenyl, which is optionally substituted once or several times by chlorine or —Y-alkylene-Z;
  c) heteroaryl; or
  d) -T-heterocyclyl;
$R^4$ is hydrogen, halogen, alkyl, alkoxy, —Y-alkylene-Z;
$R^5$ is hydrogen;
T is a single bond;
X is CH;
Y is a single bond, —O— or —S—;
Z is —NRR', —C(O)—NRR' or cyano; and
R and R' are independently hydrogen or alkyl.

Such compounds, for example, may be selected from the group consisting of:
4-Chloro-$N^1$-(4-morpholin-4-yl-phenyl)-$N^3$-(1H-pyrrolo[2,3-b]pyridin-5-yl)-isophthalamide;
4-Chloro-$N^1$-(3-morpholin-4-yl-phenyl)-$N^3$-(1H-pyrrolo[2,3-b]pyridin-5-yl)-isophthalamide hydrochloride;
4-Chloro-$N^1$-(3-pyrazol-1-yl-phenyl)-$N^3$-(1H pyrrolo[2,3-b]pyridin-5-yl)-isophthalamide hydrochloride; and
4-Chloro-$N^1$-[3-(cyano-dimethyl-methyl)-phenyl]-$N^3$-(1H-pyrrolo[2,3-b]pyridin-5-yl)-isophthalamide hydrochloride.

Another embodiment of the invention are the compounds according to formula I, wherein
$R^1$ and $R^2$ are independently chlorine or alkyl;
L is —NH—C(O)—;
Q is alkylene or cycloalkylene, preferably cycloalkylene;
n is 0;
ring A is heteroaryl;
$R^3$ is a) hydrogen;
  b) —V-phenyl, which is optionally substituted once or several times by chlorine or —Y-alkylene-Z;
  c) heteroaryl; or
  d) -T-heterocyclyl;
$R^4$ is hydrogen, halogen, alkyl, alkoxy, —Y-alkylene-Z;
$R^5$ is hydrogen;
T is a single bond;
X is CH;
Y is a single bond, —O— or —S—;
Z is —NRR', C(O)—NRR' or cyano; and
R and R' are independently hydrogen or alkyl.

Such compounds, for example, may be selected from the group consisting of:
4-Chloro-$N^3$ (1H-pyrrolo[2,3-b]pyridin-5-yl)-$N^1$-(4-trifluoromethyl-5,6,7,8-tetrahydro-quinazolin-2-yl)-isophthalamide hydrochloride;
4-Chloro-$N^1$-(6-phenoxy-pyridin-3-yl)-$N^3$-(1H-pyrrolo[2,3-b]pyridin-5-yl)-isophthalamide hydrochloride;
4-Chloro-$N^1$-(1-ethyl-3,3-dimethyl-2-oxo-2,3-dihydro-1H-indol-5-yl)-$N^3$-(1H-pyrrolo[2,3-b]pyridin-5-yl)-isophthalamide hydrochloride; and 4-Chloro-$N^1$-(4-methyl-3-oxo-3,4-dihydro-2H-benzo[1,4]thiazin-7-yl)-$N^3$-(1H-pyrrolo[2,3-b]pyridin-5-yl)-isophthalamide hydrochloride.

Another embodiment of the invention are the compounds according to formula I, wherein
$R^1$ and $R^2$ are independently chlorine or alkyl;
L is —NH—C(O)—;
Q is alkylene or cycloalkylene, preferably cycloalkylene;
n is 1;
ring A is aryl;
$R^3$ is a) hydrogen;
 b) —V-phenyl, which is optionally substituted once or several times by chlorine or —Y-alkylene-Z;
 c) heteroaryl; or
 d) -T-heterocyclyl;
$R^4$ is hydrogen, halogen, alkyl, alkoxy, —Y-alkylene-Z;
$R^5$ is hydrogen;
T is a single bond;
X is CH;
Y is a single bond, —O— or —S—;
Z is —NRR', —C(O)—NRR' or cyano; and
R and R' are independently hydrogen or alkyl.

Such a compound is for example:
4-Chloro-$N^1$-((1S,2R)-2-phenyl-cyclopropyl)-$N^3$-(1H-pyrrolo[2,3-b]pyridin-5-yl)-isophthalamide; hydrochloride.

Another embodiment of the invention are the compounds according to formula I, wherein
$R^1$ and $R^2$ are independently chlorine or alkyl;
L is —NH—C(O)—;
Q is alkylene or cycloalkylene, preferably cycloalkylene;
n is 0;
$R^3$ is a) hydrogen;
 b) —V-phenyl, which is optionally substituted once or several times by chlorine or —Y-alkylene-Z;
 c) heteroaryl; or
 d) -T-heterocyclyl;
$R^4$ is hydrogen, halogen, alkyl, alkoxy, —Y-alkylene-Z;
$R^5$ is hydrogen;
T is a single bond;
X is N;
Y is a single bond, —O— or —S—;
Z is —NRR', —C(O)—NRR' or cyano; and
R and R' are independently hydrogen or alkyl.

Another embodiment of the invention are the compounds according to formula I, wherein
L is —NH—C(O)— or —C(O)—NH—;
Q is alkylene, alkenylene or cycloalkylene; and
n is 0 or 1;
with the proviso, that if L is —NH—C(O)—, Q is not alkenylene.

Another embodiment of the invention is a process for the preparation of the compounds of formula I comprising the steps of
a) reacting a compound of formula XIIIa,

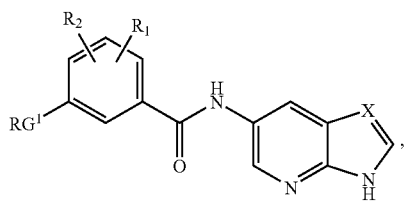

formula XIIIa wherein $R^1$, $R^2$ and X have the meaning as defined for formula I above, and $RG^1$ is either —$NH_2$ or —C(O)OH,
with a compound of formula XIVa,

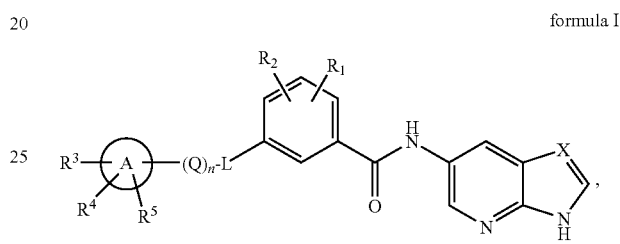

formula XIVa wherein ring A, $R^3$, $R^4$, $R^5$, Q and n have the meaning as defined for formula I above, and $RG^2$ is either —C(O)OH, if and $RG^1$ is —$NH_2$; or $RG^2$ is —$NH_2$, if and $RG^1$ is —C(O)OH,
to give the compounds of formula I, formula I wherein ring A, $R^1$, $R^2$, $R^3$, $R^4$, $R^5$, Q, n, X and L have the meaning as defined for formula I above,
b) isolating the compounds of formula I; and
c) if desired, converging the compounds of formula I into their pharmaceutically acceptable salts.

The derivatives of the general formula I or a pharmaceutically acceptable salt thereof, may be prepared by any process known to be applicable for the preparation of chemically-related compounds by the one skilled in the art. Such processes, when used to prepare the derivatives of formula I, or a pharmaceutically-acceptable salt thereof, are provided as a further feature of the invention and are illustrated by the following representative examples of schemes 1 and 2, in which, unless otherwise stated $R^1$, $R^2$, $R^3$, $R^4$, $R^5$, Q, L, X and n have the significance given herein before for formula I. Necessary starting materials may be obtained by standard procedures of organic chemistry. The preparation of such starting materials is described within the accompanying examples. Alternatively necessary starring materials are obtainable by analogous procedures to those illustrated which are within the ordinary skill of an organic chemist.

The preparation of the compounds of formula I depends on the nature of L. The compounds of formula I wherein L is —C(O)—NH— are e.g. prepared according to the following scheme 1 and are named Ia.

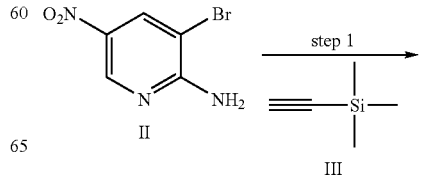

Scheme 1

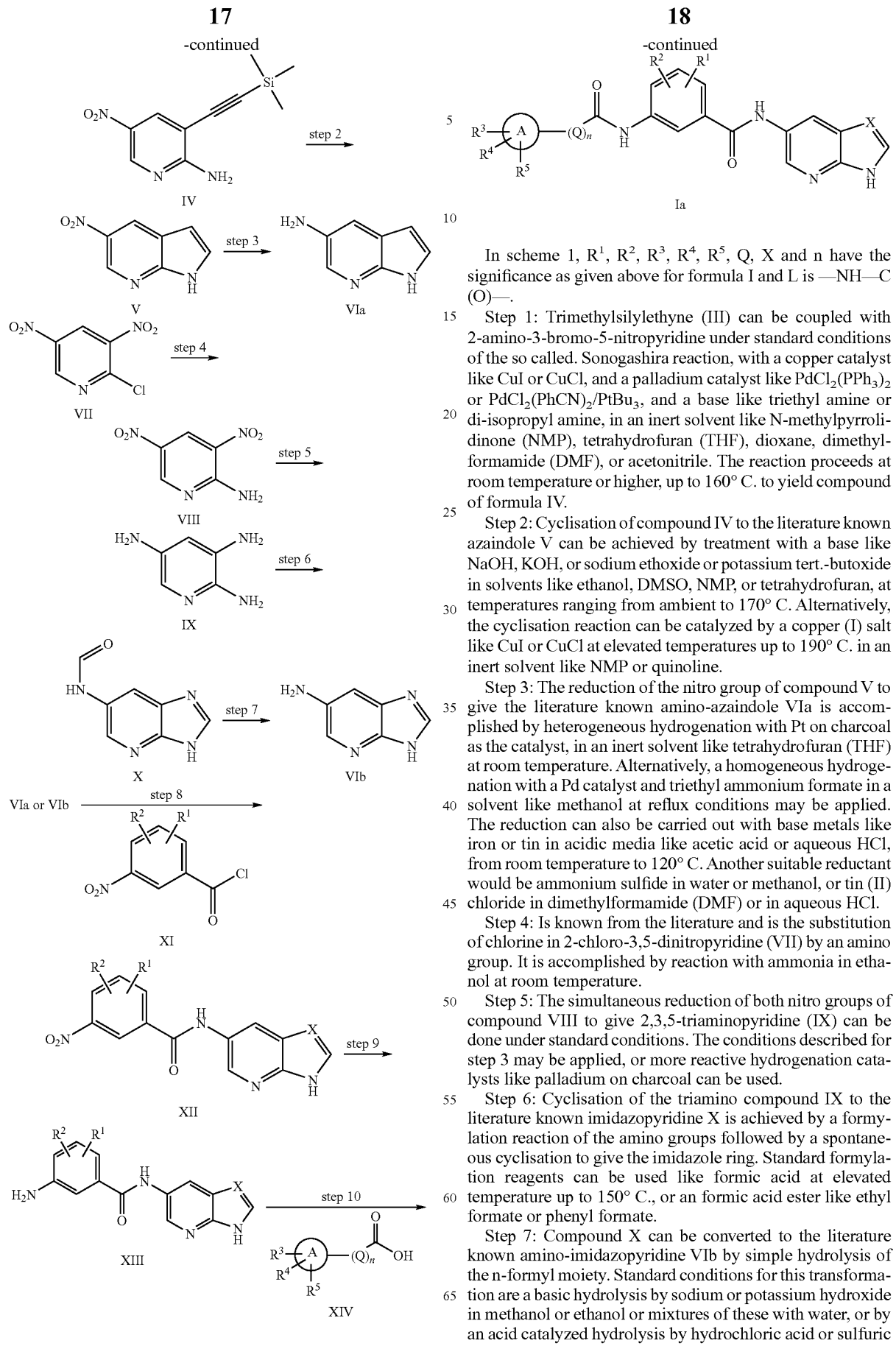

In scheme 1, $R^1$, $R^2$, $R^3$, $R^4$, $R^5$, Q, X and n have the significance as given above for formula I and L is —NH—C(O)—.

Step 1: Trimethylsilylethyne (III) can be coupled with 2-amino-3-bromo-5-nitropyridine under standard conditions of the so called. Sonogashira reaction, with a copper catalyst like CuI or CuCl, and a palladium catalyst like $PdCl_2(PPh_3)_2$ or $PdCl_2(PhCN)_2/PtBu_3$, and a base like triethyl amine or di-isopropyl amine, in an inert solvent like N-methylpyrrolidinone (NMP), tetrahydrofuran (THF), dioxane, dimethylformamide (DMF), or acetonitrile. The reaction proceeds at room temperature or higher, up to 160° C. to yield compound of formula IV.

Step 2: Cyclisation of compound IV to the literature known azaindole V can be achieved by treatment with a base like NaOH, KOH, or sodium ethoxide or potassium tert.-butoxide in solvents like ethanol, DMSO, NMP, or tetrahydrofuran, at temperatures ranging from ambient to 170° C. Alternatively, the cyclisation reaction can be catalyzed by a copper (I) salt like CuI or CuCl at elevated temperatures up to 190° C. in an inert solvent like NMP or quinoline.

Step 3: The reduction of the nitro group of compound V to give the literature known amino-azaindole VIa is accomplished by heterogeneous hydrogenation with Pt on charcoal as the catalyst, in an inert solvent like tetrahydrofuran (THF) at room temperature. Alternatively, a homogeneous hydrogenation with a Pd catalyst and triethyl ammonium formate in a solvent like methanol at reflux conditions may be applied. The reduction can also be carried out with base metals like iron or tin in acidic media like acetic acid or aqueous HCl, from room temperature to 120° C. Another suitable reductant would be ammonium sulfide in water or methanol, or tin (II) chloride in dimethylformamide (DMF) or in aqueous HCl.

Step 4: Is known from the literature and is the substitution of chlorine in 2-chloro-3,5-dinitropyridine (VII) by an amino group. It is accomplished by reaction with ammonia in ethanol at room temperature.

Step 5: The simultaneous reduction of both nitro groups of compound VIII to give 2,3,5-triaminopyridine (IX) can be done under standard conditions. The conditions described for step 3 may be applied, or more reactive hydrogenation catalysts like palladium on charcoal can be used.

Step 6: Cyclisation of the triamino compound IX to the literature known imidazopyridine X is achieved by a formylation reaction of the amino groups followed by a spontaneous cyclisation to give the imidazole ring. Standard formylation reagents can be used like formic acid at elevated temperature up to 150° C., or an formic acid ester like ethyl formate or phenyl formate.

Step 7: Compound X can be converted to the literature known amino-imidazopyridine VIb by simple hydrolysis of the n-formyl moiety. Standard conditions for this transformation are a basic hydrolysis by sodium or potassium hydroxide in methanol or ethanol or mixtures of these with water, or by an acid catalyzed hydrolysis by hydrochloric acid or sulfuric acid in mixtures of water and ethanol or methanol or dioxane. Temperatures may vary from ambient to 100° C.

Step 8: Acylation of the amino moiety on the compounds of formula VI can be done with the appropriate carboxylic acid derivatives. Preferably, isolated acid chlorides of formula XI are applied. Alternatively, in a two step procedure, the corresponding carboxylic acid becomes activated first. This reaction is carried out in an inert solvent or diluent, for example, in dichloromethane, dioxane, tetrahydrofuran (THF), N,N-dimethylfomamide (DMF), or N-methylpyrrolidone (NMP), in the presence of an activating agent. Suitable activating agents are, for example, oxalyl or thionyl chloride, isobutyl chloroformate, N-hydroxybenzotriazole, N,N'-carbonyldiimidazole, dicyclohexylcarbodiimide, N-(3-dimethylaminopropyl)-N'-ethylcarbodiimide (EDC), 2-morpholino-ethyl-isocyanide (MEI), 2-(1H-Benzotriazole-1-yl)-1,1,3,3-tetramethyluronium tetrafluoroborate (TBTU) and the like. Other activating agents can also be used and are well known to the skilled artist. The activated carboxylic acid derivative (e.g. the acid chloride of formula XI) can be sometimes isolated as intermediate. Nevertheless the reaction is often carried out in a one-pot procedure without isolation of the activated carboxylic acid intermediate. In the second step, the amine of formula VI is reacted with the appropriate activated carboxylic acid yielding the compounds of formula XII. This reaction can also be carried out in the same solvent as the activation step, or in pyridine, optionally in the presence of a base like triethyl amine or ethyl diisopropyl amine, and can be catalyzed sometimes by N,N-dimethylaminopyridine (DMAP) and the like.

If an excess of benzoyl chlorides-(XI) is used, simultaneous acylation on the heterocyclic core of XII can occur, e.g. on N-1 (X=CH) or N-1 or N-3 (X=N). Such a bis-acylated intermediate can be cleaved easily to the desired mono-acylated compound XII by subsequent treatment with ammonia in water or methanol at room temperature.

Step 9: Reduction of the nitro group can be carried out under the conditions described for step 3.

Step 10: Acylation of the free amino group in intermediates XIII is done with the appropriate carboxylic acids of formula XIV under the conditions described for step 8. If an excess of the corresponding acid chlorides is used, simultaneous acylation on the heterocyclic core of 1 can occur, e.g. on N-1 (X=CH) or N-1 or N-3 (X=N). Such a bis-acylated intermediate can be cleaved easily to the desired mono-acylated compound I by subsequent treatment with ammonia in water or methanol at room temperature.

The compounds of formula I wherein L is —NH—C(O)— are e.g. prepared according to the following scheme 2 and are named Ib.

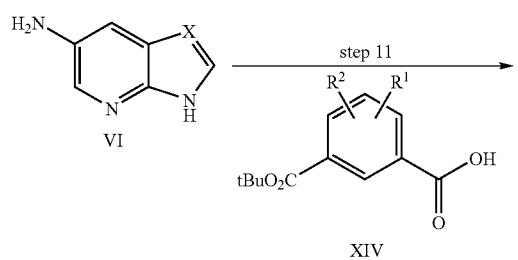

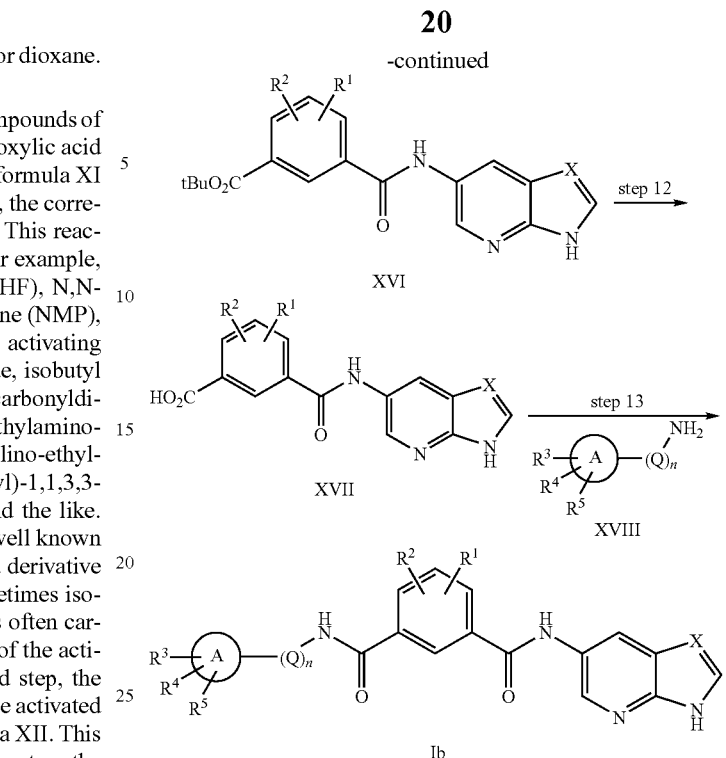

In scheme 2, $R^1$, $R^2$, $R^3$, $R^4$, $R^5$, Q, X and n have the significance as given above for formula I and L is —NH—C(O)—.

Step 11: Acylation of the amino moiety on the compounds of formula VI can be done with the appropriate carboxylic acid derivatives. Preferably, in a two step procedure, the corresponding carboxylic acid XIV becomes activated first. This reaction is carried out in an inert solvent or diluent, for example, in dichloromethane, dioxane, tetrahydrofuran (THF), N,N-dimethylformamide (DMF), or N-methylpyrrolidone (NMP), in the presence of an activating agent. Suitable activating agents are, for example, isobutyl chloroformate, N-hydroxybenzotriazole, N,N'-carbonyldiimidazole, dicyclohexylcarbodiimide, N-(3-dimethylaminopropyl)-N'-ethylcarbodiimide (EDC), 2-morpholino-ethyl-isocyanide (MEI) and the like. Other activating agents can also be used and are well known to the skilled artist. The activated carboxylic acid derivative can be sometimes isolated as intermediate. Nevertheless the reaction is often carried, out in a one-pot procedure without isolation of the activated carboxylic acid intermediate. In the second step, the amine of formula VI is reacted with the appropriate activated carboxylic acid yielding the amide compounds of formula XVI. This reaction can also be carried out in the same solvent as the activation step, or in pyridine, optionally in the presence of a base like triethyl amine or ethyl diisopropyl amine, and can be catalyzed sometimes by N,N-dimethylaminopyridine (DMAP) and the like.

If an excess of benzoic acids (XIV) is used, simultaneous acylation on the heterocyclic core of XVI can occur, e.g. on N-1 (X=CH) or N-1 or N-3 (X=N). Such a bis-acylated intermediate can be cleaved easily to the desired mono-acylated compound XVI by subsequent treatment with ammonia in water or methanol at room temperature.

Step 12: Hydrolysis of the tert.-butyl ester moiety in compounds XVI to give the free acids XVII can be done by standard procedures, preferably under acidic conditions, in an inert solvent like dichloromethane, tetrahydrofuran, or diethyl ether, optionally in the presence of water. Typical acids used in such a hydrolysis step are trifluoroacetic acid, hydrochloric acid, or sulfuric acid. Trifluoroacetic acid may also serve as the solvent.

Step 13: Conversion of the carboxylic acid intermediate XVII to the amide compounds of formula Ib is done by first activating the carboxylic acid moiety and then coupling it with amine compounds of formula XVIII. Suitable conditions are as described for step 8, scheme 1.

Certain substituents on the group $R^3$, $R^4$ and $R^5$ may not be inert to the conditions of the synthesis sequences described above and may require protection by standard protecting groups known in the art. For instance, an amino or hydroxyl group maybe protected as a tert.-butoxycarbonyl derivative. Alternatively, some substituents may be derived from others at the end of the reaction sequence. For instance, a compound of formula I may be synthesized bearing a nitro-substituent, which substituent is finally converted to an amino by standard procedures.

The compounds of formula I can contain one or several chiral centers and can then be present in a racemic, enantiomeric or diastereomeric form. The racemates can be separated according to known methods into the enantiomers. For instance, diastereomeric salts which can be separated by crystallization are formed from the racemic mixtures by reaction with an optically active acid such as e.g. D or L-camphorsulfonic acid. Alternatively separation of the enantiomers can also be achieved by using chromatography on chiral HPLC-phases (HPLC: High Performance Liquid Chromatography) which are commercially available.

Pharmaceutical compositions containing a compound of the present invention or a pharmaceutically acceptable salt thereof and a pharmaceutically acceptable carrier are an object of the present invention, as is a process for their production, which comprises bringing one or more compounds of the present invention and/or pharmaceutically acceptable salts and, if desired, one or more other therapeutically valuable substances into a galenical administration form together with one or more pharmaceutically acceptable carriers.

In accordance with the invention the compounds of the present invention as well as their pharmaceutically acceptable salts are useful in the control or prevention of illnesses. Based on their protein kinase activity, e.g. as Src, Abl or PDGFR family kinase inhibitors or as EGFR kinase inhibitor and their antiproliferative activity, said compounds are useful for the treatment of diseases such as cancer in humans or animals and for the production of corresponding pharmaceutical compositions. The dosage depends on various factors such as mariner of administration, species, age and/or individual state of health.

An embodiment of the invention is a pharmaceutical composition, containing one or more compounds according to formula I as active ingredients, together with pharmaceutically acceptable carriers.

Another embodiment of the invention is a pharmaceutical composition containing one or more compounds of formula I as active ingredients together with pharmaceutically acceptable carriers for the treatment of diseases mediated by an inappropriate activation of a Src family kinase (e.g. Src kinase).

Another embodiment of the invention is a pharmaceutical composition containing one or more compounds of formula I as active ingredients together with pharmaceutically acceptable carriers for the treatment of diseases mediated by an inappropriate activation of a Abl family kinase (e.g. Abl kinase).

Another embodiment of the invention is a pharmaceutical composition containing one or more compounds of formula I as active ingredients together with pharmaceutically acceptable carriers for the treatment of diseases mediated by an inappropriate activation of PDGFR family kinase (e.g. PDGFR alpha, PDGFR beta or CSF-IR kinase).

Another embodiment of the invention is a pharmaceutical composition containing one or more compounds of formula I as active ingredients together with pharmaceutically acceptable carriers for the treatment of diseases mediated by an inappropriate activation of EGFR kinase.

Another embodiment of the invention is a pharmaceutical composition, containing one or more compounds according to formula I as active ingredients, for the inhibition of tumor growth.

Another embodiment of the invention is a pharmaceutical composition, containing one or more compounds according to formula I as active ingredients, for the treatment of cancer.

Another embodiment of the invention is a pharmaceutical composition containing one or more compounds of formula I as active ingredients together with pharmaceutically acceptable carriers for the treatment of colorectal, breast, lung, prostate, pancreatic, gastric, bladder, ovarian, melanoma, neuroblastoma, cervical, kidney or renal cancers, leukemias or lymphomas.

Another embodiment of the invention is the use of a compound according to formula I, for the manufacture of corresponding pharmaceutical compositions for the inhibition of tumor growth.

Another embodiment of the invention is the use of a compound according to formula I, for the manufacture of corresponding pharmaceutical compositions for the treatment of colorectal, breast, lung, prostate, pancreatic, gastric, bladder, ovarian, melanoma, neuroblastoma, cervical, kidney or renal cancers, leukemias or lymphomas.

Another embodiment of the invention is the use of the compounds of formula I as anti-proliferating agents.

Another embodiment of the invention is the use of one or more compounds of formula I for the treatment of cancer.

Another embodiment of the invention is a method of treating cancer comprising administering to a person in need thereof a therapeutically effective amount of a compound of formula I.

Another embodiment of the invention is a method of treating cancer comprising administering to a person in need thereof a therapeutically effective amount of a compound of formula I, wherein the cancer is colorectal cancer, breast cancer, lung cancer, prostate cancer, pancreatic cancer, gastric cancer, bladder cancer, ovarian cancer, melanoma, neuroblastoma, cervical cancer, kidney cancer or renal cancer, leukemia, or lymphoma.

The compounds according to the present invention may exist in the form of their pharmaceutically acceptable salts. The term "pharmaceutically acceptable salt" refers to conventional acid-addition salts that retain the biological effectiveness and properties of the compounds of formula I and are formed from suitable non-toxic organic or inorganic acids. Sample acid-addition salts include those derived from inorganic acids such as hydrochloric, acid, hydrobromic acid, hydroiodic acid, sulfuric acid, sulfamic acid, phosphoric acid and nitric acid, and those derived from organic acids such as p-toluenesulfonic acid, naphthalenesulfonic acid, naphthalenedisulfonic acid, methanesulfonic acid, ethanesulfonic acid, citric acid, ascorbic acid and the like. The chemical modification of a pharmaceutical compound (i.e. a drug) into a salt is a technique well known to pharmaceutical chemists to obtain improved physical and chemical stability, hygroscopicity, flowability and solubility of compounds. See, e.g. Stahl, P. H., and Wermuth, G., (editors), Handbook of Pharmaceutical Salts, Verlag Helvetica Chimica Acta (VHCA), Zürich, (2002), or Bastin, R. J., et al., Organic Proc. Res. Dev. 4 (2000) 427-435.

Pharmacological Activity

The compounds of formula I and their pharmaceutically acceptable salts possess valuable pharmacological properties. It has been found that said compounds show activity as inhibitors of Src, Abl and PDGFR kinases and also show anti-proliferative activity. Consequently the compounds of the present invention are useful in the therapy and/or prevention of illnesses with known over-expression of Src, Abl and PDGFR kinases, especially in the therapy and/or prevention of illnesses mentioned above. The activity of the present compounds as inhibitors of Src, Abl and PDGFR kinase are demonstrated by the following biological assays:

IC50 Determination for Inhibitors of Src Kinase

Src assay was done using mouse full-length Src protein, fluorescein labeled peptide substrate (with a sequence of KVEKIGEGTYGVVYK) and quantified by Molecular Devices' IMAP fluorescence polarization technology. Compounds were tested in serially diluted concentrations in 384 well plates. Kinase reaction was performed in KAB Buffer (10 mM HEPES, pH 7, 50 mM NaCl, 5 mM $MgCl_2$, 1 mM DTT, 0.1 mM $NaVO_4$, 0.02% BSA), in the presence of 24 uM ATP, incubated at 37° C. for 60 minutes. Reaction was stopped by IMAP bead mix (at 1:400 dilution). After incubation at room temperature for 2 hours, the reaction product was analyzed on LJL Acquest (excitation 485 nM and Emission 530 nM).

FP reading (in mP) was used to calculate reaction rate. The assay was semi-automated by Tomtec Quadra workstation. The results are shown in Table 1.

TABLE 1

| Example No. | IC50 Src kinase inhibition [µM] |
|---|---|
| 6-1 | 0.010 |
| 2-3 | 0.189 |
| 1-1, 2-1, 2-2, 3-1, 4-2, 4-3, 4-5, 5-6, 6-2, 6-3, 7-1 | 0.005-1.000 |

IC50 Determination for Inhibitors of Abl Kinase

Abl assay was done using fusion protein corresponding to mouse Abl (27-end), fluorescein labeled peptide substrate (with a sequence of EAIYAAPFAKKK) and quantified by Molecular Devices' IMAP fluorescence polarization technology. Compounds were tested in serially diluted concentrations in 384 well plates. Kinase reaction was performed in KAB Buffer (10 mM HEPES, pH 7, 50 mM NaCl, 5 mM $MgCl_2$, 1 mM DTT, 0.1 mM $NaVO_4$, 0.02% BSA), in the presence of 22.8 uM ATP, incubated at 37° C. for 60 minutes. Reaction was stopped by IMAP bead mix (at 1:400 diluted). After incubation at room temperature for 3 hours, the reaction product was analyzed on LJL Acquest (excitation 485 nM and Emission 530 nM).

FP reading (in mP) was used to calculate reaction rate. The assay was semi automated by Tomtec Quadra workstation. The results are shown in Table 2.

TABLE 2

| Example No. | IC50 Abl kinase inhibition [µM] |
|---|---|
| 2-2 | 0.063 |
| 7-1 | 0.831 |
| 1-1, 2-1, 2-3, 4-1, 4-2, 4-3, 4-5, 4-6, 6-1 | 0.005-1.000 |

IC50 Determination for Inhibitors of PDGFR Kinase

Assay Principle

PDGFR assay was carried out with human recombinant PDGFR beta, fluorescein labeled peptide substrate (with a peptide sequence of ALTSNQEYLDLSMPL) and test compounds (in serial dilution) using 384-well plates. Kinase reaction was performed in MOPS buffer (20 mM MOPS pH 7.1, 5 mM Sodium Acetate, 6.25 mM $MgCl_2$, 0.5 mM EDTA, 1 mM DTT, 0.04 mM $NaVO_4$, 0.02% BSA), in the presence of 48 uM ATP, incubated at room temperature for 60 minutes. Reaction was stopped by IMAP Bead Binding System (Molecular Devices). After incubation at room temperature for 2 hours, the reaction product was analyzed on LJL Acquest.

FP reading (in mP) was used to calculate reaction rate. The assay was semi-automated by Tomtec Quadra workstation. The results are shown in Table 3.

TABLE 3

| Example No. | IC50 PDGFR kinase inhibition [µM] |
|---|---|
| 2-1 | 0.014 |
| 6-2 | 1.119 |
| 1-1, 2-2, 2-3, 7-1 | 0.01-1.000 |

Antiproliferative Activity

The activity of the present compounds us antiproliferative agents is demonstrated by the following biological assay:

CellTiter-Glo™ Assay in HCT 116 Cells

The CellTiter-Glo™ Luminescent Cell Viability Assay (Promega) is a homogeneous method of determining the number of viable cells in culture based on quantitation of the ATP present, which signals the presence of metabolically active cells.

HCT 116 cells (human colon carcinoma, ATCC-No. CCl-247) were cultivated in RPMI 1640 medium with GlutaMAX™ 1 (Invitrogen, Cat-No. 61870-010), 5% Fetal Calf Serum (FCS, Sigma Cat-No. F4135 (FBS)); 100 Units/ml penicillin/100 µg/ml streptomycin (=Pen/Strep from Invitrogen Cat. No. 15140). For the assay the cells were seeded in 384 well plates, 1000 cells per well, in the same medium. The next day the test compounds were added in various concentrations ranging from 30 µM to 0.0015 µM (10 concentrations, 1:3 diluted). After 5 days the CellTiter-Glo™ assay was done according to the instructions of the manufacturer (Cell-Titer-Glo™ Luminescent Cell Viability Assay, from Promega). In brief: the cell-plate was equilibrated to room temperature for approximately 30 minutes and than the Cell-Titer-Glo™ reagent was added. The contents were carefully mixed for 15 minutes to induce cell lysis. After 45 minutes the luminescent signal was measured in Victor 2, (scanning multiwell spectrophotometer, Wallac).

Details:

1st. Day:

Medium: RPMI 1640 with GlutaMAX™ 1 (Invitrogen, Cat-No. 61870), 5% FCS (Sigma Cat.-No. F4135), Pen/Strep (Invitrogen, Cat No. 15140).

HCT116 (ATCC-No. CCl-247): 1000 cells in 60 µl per well of 384 well plate (Greiner 781098, µClear-plate white)
After seeding incubate plates 24 h at 37° C., 5% $CO_2$ 2nd. Day: Induction (Treatment with Compounds, 10 Concentrations):

In order to achieve a final concentration of 30 µM as highest concentration 3.5 µl of 10 mM compound stock solution were added directly to 163 µl media. Then step e) of the dilution procedure described below, was followed.

In order to achieve the second highest to the lowest concentrations, a serial dilution with dilution steps of 1:3 was followed according to the procedure (a-e) as described here below:

a) for the second highest concentration add 10 µl of 10 mM stock solution of compound to 20 µl dimethylsulfoxide (DMSO)
b) dilute 8×1:3 (always 10 µl to 20 µl DMSO) in this DMSO dilution row (results in 9 wells with concentrations from 3333.3 µM to 0.51 µM)
c) dilute each concentration 1:47.6 (3.5 µl compound dilution to 163 µl media)
d) add 10 µl of every concentration to 60 µl media in the cell plate resulting in final concentration of DMSO:0.3% in every well and resulting in 10 final concentration of compounds ranging from 30 µM to 0.0015 µM.

Each compound is tested in triplicate.
Incubate 120 h (5 days) at 37° C., 5% $CO_2$ Analysis:
Add 30 µl CellTiter-Glo™ Reagent (prepared from CellTiter-Glo™ Buffer and CellTiter-Glo™ Substrate (lyophilized) purchased from Promega) per well,
shake 15 minutes at room temperature
incubate further 45 minutes at room temperature without shaking Measurement:
Victor 2 scanning multiwell spectrophotometer (Wallac), Luminescence mode (0.5 sec/read, 477 nm)
Determine IC50 using a non-linear curve fit (XLfit software (ID Business Solution Ltd., Guilford, Surrey, UK))

With all compounds a significant inhibition of HCT 116 cell viability was detected, which is exemplified by the compounds shown in Table 4.

TABLE 4

| Example No. | IC50 HCT 116 [µM] |
|---|---|
| 1-1 | 1.81 |
| 4-5 | 0.38 |
| 1-2, 2-1, 2-2, 2-3, 4-1, 4-3, 4-4, 4-6, 4-7, 8-1, 8-2, 8-3, 8-5, 8-7, 8-8 | 0.10-10.00 |

The compounds according to this invention and their pharmaceutically acceptable salts can be used as medicaments, e.g. in the form of pharmaceutical compositions. The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically inert, inorganic or organic carriers. Lactose, corn starch or derivatives thereof, talc, stearic acids or it's salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

A pharmaceutical compositions comprise e.g. the following:
a) Tablet Formulation (Wet Granulation):

| Item | Ingredients | Mg/tablet | | | |
|---|---|---|---|---|---|
| 1. | Compound of formula I | 5 | 25 | 100 | 500 |
| 2. | Lactose Anhydrous DTG (direct tabletting grade) | 125 | 105 | 30 | 150 |
| 3. | Sta-Rx 1500 (pre-gelatinized starch powder) | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

b) Capsule Formulation:

| Item | Ingredients | Mg/capsule | | | |
|---|---|---|---|---|---|
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

c) Micro Suspension:
1. Weigh 4.0 g glass beads in custom made tube GL 25, 4 cm (the beads fill half of the tube).
2. Add 50 mg compound, disperse with spatulum and vortex.
3. Add 2 ml gelatin solution (weight beads: gelatin solution=2:1) and vortex.
4. Cap and wrap in aluminum foil for light protection.
5. Prepare a counter balance for the mill.
6. Mill for 4 hours, 20/s in a Retsch mill (for some substances up to 24 hours at 30/s).
7. Extract suspension from beads with two layers of filter (100 µm) on a filter holder, coupled to a recipient vial by centrifugation at 400 g for 2 min.
8. Move extract to measuring cylinder.

9. Repeat washing with small volumes (here 1 ml steps) until final volume is reached or extract is clear.
10. Fill up to final volume with gelatin and homogenize.

The following examples are provided to aid the understanding of the present invention, the true scope of which is set forth in the appended claims. It is understood that modifications can be made in the procedures set forth without departing from the spirit of the invention.

Experimental Procedures

Starting Materials

Example a

5-Nitro-3-trimethylsilanylethynyl-pyridin-2-ylamine 12.0 g 2-Amino-3-bromo-5-nitropyridine, 1.93 g dichlorobis(triphenyl-phosphine)palladium(II) and 0.524 g copper (I) iodide were dispersed under nitrogen in 60 ml dry tetrahydrofuran (THF). 7.03 g trimethylsilylacetylene and 16.71 g triethylamine were added and the mixture was stirred 16 hours (hrs) at room temperature (RT). The mixture was filtered, the filtrate was evaporated and the residue purified by chromatography on silica in ethyl acetate/heptane mixtures.
Yield 12.2 g Example b 5-Nitro-1H-pyrrolo[2,3-b]pyridine To a solution of 500 mg 5-Nitro-3-trimethylsilanylethynyl-pyridin-2-ylamine in 4 ml ethanol were added 93.5 mg sodium hydroxide, and the mixture was stirred under irradiation in a microwave-oven for 30 minutes (min) at 140° C. 20 equal batches of this kind were combined and evaporated. The residue was dissolved in 100 ml conc. hydrochloric acid and stirred for 30 min at RT. It was again evaporated and the residue was refluxed with THF for 30 min. Insoluble parts were removed by filtration, the filtrate was evaporated and the residue was chromatographed on silica in ethyl acetate/heptane mixtures.
Yield 2.30 g Example c 1H-Pyrrolo[2,3-b]pyridin 5-ylamine 2.675 g 5-Nitro-1H-pyrrolo[2,3-b]pyridine in 200 ml THF were hydrogenated over 1.0 g Platinum on carbon at atmospheric pressure for 3 hrs at RT (with thin layer chromatography (TLC) control). The catalyst was removed by filtration, the filtrate was evaporated and the residue purified by chromatography on silica in ethyl acetate/heptane mixtures.
Yield 1.84 g Example d 2-Chloro-5-nitro-N-(1H-pyrrolo[2,3-b]pyridin-5-yl)-benzamide 1.87 g 1H-Pyrrolo[2,3-b]pyridin-5-ylamine in 60 ml dry pyridine were treated dropwise at RT with a solution of 6.79 g 2-chloro-5-nitrobenzoyl chloride in 10 ml dichloromethane. Stirring was continued over night. The mixture was evaporated and the residue was treated with 25 ml methanol and 10 ml conc. ammonia for 2 hrs at RT. The solvents are again evaporated and the residue is dispersed in water. The crude product is isolated by filtration and washed thoroughly with water and diethylether.
Yield 3.85 g Example e 5-Amino-2-chloro-N-(1H-pyrrolo[2,3-b]pyridin-5-yl)-benzamide 3.85 g 2-Chloro-5-nitro-N-(1H-pyrrolo[2,3-b]pyridin-5-yl)-benzamide in 600 ml THF were hydrogenated over 2.5 g platinum on carbon at atmospheric pressure over night at RT. The catalyst was removed by filtration and the filtrate evaporated. The residue was purified by chromatography on silica eluting first with ethyl acetate and finally ethyl acetate/methanol mixtures.
Yield 2.06 g Example f 2-Amino-3,5-dinitropyridine To a solution of 25 g 2-Chloro-3,5-dinitropyridine in 190 ml ethanol were added dropwise 75 ml concentrated ammonia at room temperature. After stirring for 1 hour (hr), the mixture was cooled in an ice bath. The product was isolated by filtration and washed with cold water.
Yield 22.1 g of the title product Example g 2,3,5-triaminopyridine 5 g 2-Amino-3,5-dinitropyridine in a mixture of 66 ml methanol and 33 ml THF were hydrogenated over 800 mg 10% palladium on charcoal at room temperature and atmospheric pressure. After the calculated amount of hydrogen was consumed, the catalyst was filtered off and the filtrate was concentrated under vacuum yielding 3.31 g of the crude product which was used for the next step without further purification.

Example h

N-(3H-Imidazo[4,5-b]pyridin-6-yl)-formamide 3.1 g of 2,3,5-triaminopyridine in 150 ml formic acid were stirred at 110° C. for 16 hrs. The mixture was evaporated to dryness under vacuum to yield 4.17 g of the crude title product.

Example i

3H-Imidazo[4,5-b]pyridin-6-ylamine hydrochloride salt 4.17 g of N-(3H-Imidazo[4,5-b]pyridin-6-yl)-formamide in 100 ml methanol and 100 ml concentrated hydrochloric acid were stirred 1 hr at 60° C. The solvents were evaporated and the residue dried to yield 4.3 g of the title product.

Example j

N-(3H-Imidazo[4,5-b]pyridin-6-yl)-2-methyl-5-nitro-benzamide 1.0 g of 3 1 1-Imidazo[4,5-b]pyridin-6-ylamine hydrochloride salt in 1.0 ml dry N,N-dimethylformamide (DMF) and 2 ml dry pyridine were treated dropwise at room temperature with 2.34 g 2-methyl-5-nitrobenzoyl chloride. After 3 hrs the solvents were removed under vacuum and the residue stirred 1 hr in a mixture of 10 ml methanol and 10 ml concentrated ammonia. 20 ml water were added the mixture was concentrated under vacuum at 40° C. The product precipitated and was collected by filtration and washed with dilute ammonia.
Yield 750 mg after drying.

Example k

5-Amino-N-(3H-imidazo[4,5-b]pyridin-6-yl)-2-methyl-benzamide 0.75 g of N-(3H-Imidazo[4,5-b]pyridin-6-yl)-2-methyl-5-nitro-benzamide in 20 ml methanol were hydrogenated over 10% palladium on charcoal at room temperature and atmospheric pressure. After 3 hrs conversion was complete as judged by HPLC/MS and the catalyst was filtered off. The filtrate was evaporated and the residue was used without further purification for the next steps.
Yield 0.51 g

Example l

4-Chloro-isophthalic acid 1 tert-butyl ester 5.34 g 3-bromo-4-chlorobenzoic acid tert-butyl ester in 60 ml dry THF were cooled to −78° C. 12.59 ml (1.1 equivalents) of a 1.6 M solution of n-butyl lithium in hexane were added slowly and stirring was continued at −78° C. for 30 min. 20 g solid carbon dioxide were quickly crushed and added to the mixture. Cooling was continued for another 30 min before the mixture was allowed to warm up to room temperature. After 1 hr at room temperature, water and ethyl acetate were added and the organic phase was separated. The water phase was extracted with ethyl acetate and the combined organic phases were evaporated and purified by chromatography on silica in a heptane/ethyl acetate gradient.
Yield 2.82 g of the title product.

Example m

4-Chloro-N-(1H-pyrrolo[2,3-b]pyridin-5-yl)-isophthalamic acid tert-butyl ester 4.16 g 4 Chloro-isophthalic acid 1-tert-butyl ester in 10 ml dry DMF were stirred with 2.63 g carbonyldiimidazole for 1 hr at room temperature. 1.80 g 1H-Pyrrolo[2,3-b]pyridin-5-ylamine and 10 mg 4-dimethylaminopyridine were added and the mixture was heated to 60° C. After 4 hrs, the solvent was removed under vacuum and the residue was dissolved in a mixture of 5 ml methanol and 5 ml concentrated ammonia. After stirring for 20 min at room temperature, the mixture was again evaporated and the residue purified by chromatography on silica in ethyl acetate/heptane mixtures.
Yield 3.00 g of the title product.

Example n

4-Chloro-N-(1H-pyrrolo[2,3-b]pyridin-5-yl)-isophthalamic acid

To 45 mg 4-Chloro-N-(1H-pyrrolo[2,3-b]pyridin-5-yl)-isophthalamic acid tert-butyl ester in 1 ml dichloromethane were added 1 ml trifluoroacetic acid at room temperature. Stirring was continued for 2 hrs and the mixture was evaporated under vacuum to give 28 mg of the title product.

Substituted carboxylic acids XIV which are not commercially available were prepared according to the following procedures:

Example o 2 (3-Bromo-phenylsulfanyl)-propionamide

To a mixture of 5.0 g 3-bromobenzenethiol and 5.96 g potassium carbonate in 50 ml DMF were added 3.86 g 2-bromopropionamide at RT. The mixture was warmed up and stirred at 70° C. for 3.5 hrs. After cooling, 200 ml water were added and the mixture extracted 3 times with dichloromethane. Drying and evaporation of the organic phases yielded 6.5 g of the title product which was used without further purification.

Example p-1

3'-(1-Carbamoyl-ethylsulfanyl)-biphenyl-4 carboxylic acid 3.0 g 2-(3-Bromo-phenylsulfanyl)-propionamide, 1.95 g of 4-carboxybenzene-boronic acid, and 8.05 g potassium carbonate were stirred in a mixture of 25 ml dioxane and 25 ml water. 1.35 g tetrakis-triphenylphosphino-palladium were added under nitrogen atmosphere and the mixture was heated 85 C for 14 hrs. The mixture was diluted with 40 ml water and filtered. The filtrate was adjusted to pH 2 with conc. HCl and the precipitated product isolated by filtration.
Yield 2.8 g

Example p-2

3'-(2-Dimethylamino-ethoxy)-biphenyl-4-carboxylic acid

3'-(2-Dimethylamino-ethoxy)biphenyl-4-carboxylic acid was prepared analogously to example p-1, starting from [2-(3-Bromo-phenoxy)-ethyl]-dimethyl-amine.

Example q 1-(3-Bromo-benzyl)-4-methyl-piperazine 0.30 g 1-Methylpiperazine in 2 ml THF were treated dropwise at RT with a solution of 0.5 g 3-bromobenzyl bromide in 3 ml THF. After stirring for 2 hrs, the mixture was heated to 60 C for 30 min. The solvent was evaporated and the residue chromatographed on silica using a gradient from heptane to heptane/dichloromethane/conc. ammonia (4/6/0.5).
Yield 0.16 g of the title product

Example r

3'-(4-Methyl-piperazin-1-ylmethyl)-biphenyl-4-carboxylic acid 98 mg 4-Carboxybenzeneboronic acid, 159 mg 1-(3-Bromo-benzyl)-4-methyl-piperazine, 410 mg potassium carbonate, and 69 mg tetrakis-triphenylphosphino-palladium were stirred under an argon atmosphere in a mixture of 1 ml dioxane and 1 ml water at 85 C for 16 hrs. The mixture was cooled to RT, diluted with 100 ml water and filtered. The filtrate was carefully treated with conc. HCl until the product precipitated. Filtration and drying of the residue yielded 190 mg of the title product.

Example s

3'-(1-Carbamoyl-ethylsulfanyl)-biphenyl-4-carboxylic acid 1.0 g 2 (3-Bromo-phenoxy)-ethyl]-dimethyl-amine, 0.694 g of 4-carboxy-benzeneboronic acid, and 2.86 g potassium carbonate were stirred in a mixture of 5 ml dioxane and 5 ml water. 0.478 g tetrakis-triphenylphosphino-palladium were added under nitrogen atmosphere and the mixture was heated 85 C for 14 hrs. The mixture was diluted with 15 ml water and filtered. The filtrate was adjusted to pH 2 with conc. HCl and the precipitated product isolated by filtration.
Yield 1.06 g Example t 3-(1-Cyano-ethyl)-benzoic acid ethyl ester To a solution of 700 mg 3-(1-Cyano-ethyl)-benzoic acid in 20 ml dichloromethane were added dropwise 610 mg oxalyl chloride and 2 drops of DMF at RT. After stirring for 1 hr, 10 ml ethanol were added and stirring was continued for another hr. The solvents were evaporated, the residue dissolved in dichloromethane and washed with aqueous sodium bicarbonate solution. The dichloromethane phase was dried, evaporated and the residue purified by chromatography on silica in ethyl acetate/heptane mixtures.
Yield 570 mg.

Example u 3-(1-Cyano-1-methyl-ethyl)-benzoic acid ethyl ester 3-(1-Cyano-ethyl)-benzoic acid ethyl ester were dissolved in 4 ml dry DMF. Under nitrogen atmosphere, 138 mg of 60% sodium hydride and 423 mg methyl iodide were added at RT. The mixture was stirred for 16 hrs, then quenched by addition of 1 ml methanol and evaporated. The residue was purified by chromatography on silica in ethyl acetate/heptane mixtures.
Yield 300 mg.

Example v 3-(1-Cyano-1-methyl-ethyl)-benzoic acid

A mixture of 300 mg 3-(1-Cyano-1-methyl-ethyl)-benzoic acid ethyl ester and 165 mg sodium hydroxide in 1 ml ethanol and 0.5 ml water were stirred 2 hrs at RT. 20 ml water were added and the pH was adjusted to 1-2 by addition of conc. hydrochloric acid. The title product precipitated and was isolated by filtration, washed with water and dried, yielding 184 mg.

Example w

3-Pyrimidin-5-yl-acrylic acid 4.25 g 5-bromopyrimidine, 8.83 g tert.-butyl acrylate, 900 mg palladium (II) acetate, 1.79 g triphenylphosphane and 351 mg triethylamine were charged to a closed glass vial and heated with stirring to 80° C. over night. The mixture was evaporated under vacuum, the residue dissolved in ethyl acetate and filtered over a pad of silica. The filtrate was evaporated to yield 2.0 g of crude 3-pyrimidin-5-yl-acrylic acid tert.-butyl ester.

The crude tert.-butyl ester was dissolved in 20 ml dichloromethane and 10 ml trifluoroacetic acid were added at room temperature. After stirring over night the mixture was evaporated under vacuum and the residue purified by chromatography on silica in a gradient of ethyl acetate and methanol.
Yield 143 mg of the title product.

Substituted amines XVIII which are not commercially available were prepared:

Example x 2-(3-Bromo-phenyl)-2-methyl-propionitrile 257 mg 95% sodium hydride were stirred at room temperature in 25 ml dry DMF under an atmosphere of nitrogen. A solution of 1 g 3-bromophenylacetonitrile and 1.593 g iodomethane in 10 ml dry diethyl ether was added slowly below 30° C. The mixture was stirred over night at room temperature and then quenched by addition of a small amount of water. The solvents were evaporated under vacuum and the residue was purified by chromatography on silica in a heptane/ethyl acetate gradient.
Yield 0.97 g of the title product.

Example y 2-(3-Ammo-phenyl)-2-methyl-propionitrile 1.0 g 2-(3 Bromo phenyl)-2-methyl-propionitrile, 204 mg tris(dibenzylidene-acetone)dipalladium(0) and 156 mg (biphenyl-2-yl)dicyclohexylphosphine were dissolved in 10 ml dry THF and thoroughly degassed and purged with nitrogen. 10.7 ml of a 1 M solution of lithium bis(trimethylsilyl)amide in THF was added and the mixture was stirred at 65° C. for 18 hrs. Water and ethyl acetate were added and the organic phase separated. The water phase was extracted with ethyl acetate, and the combined organic phases were dried, evaporated and purified by chromatography on silica in a heptane/ethyl acetate gradient.
Yield 481 mg of the title product.

Example z

5-Amino-1-ethyl-3,3-dimethyl-1,3-dihydro-indol-2-one was prepared as described in WO 91/06545 and Mertens, A., et al., J. Med. Chem. 30 (1987) 1279-1287.

Example z-a

7-Amino-4-methyl-4H-benzo[1,4]thiazin-3-one was prepared as described in WO 2004/041823.

Final Products

Example 1-1

3'-(2-Dimethylamino-ethoxy)-biphenyl-4-carboxylic acid[4-chloro-3-(1H-pyrrolo[2,3-b]pyridin]pyridin-5-ylcarbamoyl)-phenyl]-amide To 150 mg 3'-(2-Dimethylamino-ethoxy)-biphenyl-4-carboxylic in 4 ml dry DMF were added 114 mg N'-(3-dimethylaminopropyl)-N-ethylcarbodiimide hydrochloride and 60 mg 4-dimethylaminopyridine. The mixture was stirred 30 min at 50° C., then cooled to room temperature. 158 mg of 5-Amino-2-chloro-N-(1H-pyrrolo[2,3-b]pyridin-5-yl)-benzamide (from example e) in 2 ml DMF were added, and the mixture again heated to 50° C. over night. The solvent was evaporated, the residue dissolved in a small amount of methanol and purified by chromatography on reversed phase C-18 silica in a water methanol gradient.

Yield 12 mg of the title product.

$^1$H-NMR (400 MHz, D$_6$-DMSO): δ=11.62 (br, 1H), 10.57 (s, 2H), 8.40 (d, 2H), 8.07 (d, 3H), 7.99 (d, 1H), 7.88 (d, 2H), 7.58 (d, 1H), 7.48 (m, 1H), 7.4.1 (m, 1H), 2.36-7.25 (m, 2H), 7.01 (d, 1H), 6.47 (d, 1H), 4.15 (t, 2H), 2.65 (t, 2H), 2.23 (s, 6H)

MS (ESI−): m/z=552.24

Example 1-2

The following example was prepared analogously to the procedure described for Example 1-1, using the appropriate starting materials.

| Example No. | Systematic Name | $^1$H-NMR (400 MHz, D$_6$-DMSO) | MS (Method) |
|---|---|---|---|
| 1-2 | 3'-(1-Carbamoyl-ethylsulfanyl)-biphenyl 4 carboxylic acid [4-chloro 3 (1H-pyrrolo[2,3-b]pyridin-5-ylcarbamoyl)-phenyl]-amide | δ = 11.62 (br, 1H), 10.58 (s, 1H), 10.56 (s, 1H), 8.43 (s, 1H), 8.40 (m, 1H), 8.14-8.06 (m, 3H), 7.99 (m, 1H), 7.90-7.84 (d, 1H), 7.76 (s, 1H), 7.65 (d, 1H), 7.59 (d, 1H), 7.55 (s, 1H), 7.51-7.42 (m, 3H), 7.12 (br, 2H), 6.48 (m, 1H), 3.99 (q, 1H), 1.40 (d, 3H) | 570.22 (ESI+) |

Example 2-1

Biphenyl-3-carboxylic acid[4-chloro-3-(1H-pyrrolo[2,3-b]pyridin-5-ylcarbamoyl)-phenyl]-amide 500 mg biphenyl-3-carboxylic acid were dissolved in 10 ml dichloromethane and one drop of DMF was added. 385 mg oxalyl chloride were added dropwise at room temperature and stirring was continued for 2 hrs. The solvent was evaporated. 166 mg of the above residue were added to a solution of 100 mg 5-Amino-2-chloro-N-(1H-pyrrolo[2,3-b]pyridin-5-yl)-benzamide (from example e) in 2 ml dry pyridine at room temperature. The mixture was stirred over night, evaporated, and the residue taken up in 3 ml methanol and 1 ml concentrated ammonia. After stirring for 1 hr at room temperature, the solvents were again evaporated and the residue dispersed in water. The product was isolated by filtration and washed thoroughly with water and subsequently with diethyl ether.

Yield 84 mg of the title product.

$^1$H-NMR (400 MHz, D$_6$-DMSO): δ=11.62 (br, 1H), 10.58 (br, 2H), 8.40 (d, 2H), 8.26 (s, 1H), 8.11-7.85 (m, 4H), 7.78 (m, 2H), 7.70-7.37 (m, 6H), 6.48 (s, 1H)

MS (ESI+): m/z=467.25

Examples 2-2 to 2-8

The following examples were prepared analogously to the procedure described for Example 2-1, using the appropriate starting materials.

| Example No. | Systematic Name | $^1$H-NMR (400 MHz, D$_6$-DMSO) | MS (Method) |
|---|---|---|---|
| 2-2 | Biphenyl-4-carboxylic acid [4-chloro-3-(1H-pyrrolo[2,3-b]pyridin-5-ylcarbamoyl)-phenyl]-amide | d = 11.52 (br, 1H), 10.57 (br, 2H), 8.34-8.26 (m, 2H), 8.02-7.96 (m, 3H), 7.89 (m, 1H), 7.78 (d, 2H), 7.68 (d, 2H), 7.48 (d, 1H), 7.45-7.30 (m, 4H), 6.37 (m, 1H) | 467.29 (ESI+) |
| 2-3 | 2-Chloro-5-(4-morpholin-4-yl-benzoylamino)-N-(1H-pyrrolo[2,3-b]pyridin-5-yl)-benzamide | d = 11.61 (br, 1H), 10.54 (br, 1H), 10.22 (br, 1H), 8.42 (m, 1H), 8.38 (m, 1H), 8.05 (m, 1H), 7.96 (m, 1H), 7.92 (m, 2H), 7.53 (d, 1H), 7.48 (m, 1H), 7.05 (d, 2H), 6.47 (m, 1H), 3.76 (t, 4H), 3.27 (t, 4H) | 476.32 (ESI+) |
| 2-4 | 2-Chloro-5-((E)-3-phenyl-but-2-enoylamino)-N-(1H-pyrrolo[2,3-b]pyridin-5-yl)-benzamide | d = 11.61 (br, 1H), 10.53 (br, 1H), 10.38 (br, 1H), 8.42 (d, 1H), 8.37 (d, 1H), 7.96 (d, 1H), 7.75 (m, 1H), 7.61-7.37 (m, 7H), 6.47 (m, 1H), 6.43 (d, 1H), 2.57 (s, 3H) | 431.09 (ESI+) |
| 2-5 | 2-Chloro-5-{3-[4-(3-dimethylamino-propoxy)-phenyl]-acryloylamino}-N-(1H-pyrrolo[2,3-b]pyridin-5-yl)-benzamide | d = 11.60 (br, 1H), 10.54 (s, 1H), 10.41 (s, 1H), 8.42 (m, 1H), 8.37 (m, 1H), 7.69 (d, 1H), 7.81 (m, 1H), 7.62-7.50 (m, 4H), 7.48 (m, 1H), 7.00 (d, 2H), 6.67 (d, 1H), 6.47 (m, 1H), 4.05 (t, 2H), 2.38 (t, 2H), 2.17 (s, 6H), 1.86 (m, 2H) | 516.13 (ESI−) |
| 2-6 | 2-Chloro-5-[3-(3-cyano-phenyl)-2-methyl-acryloylamino] N | d = 11.61 (br, 1H), 10.53 (s, 1H), 10.25 (s, 1H), 8.39 (m, 2H), 7.98 (m, 1H), 7.93 (m, 1H), 7.89 (m, 1H), 7.82 (m, | 456.12 (ESI+) |

| Example No. | Systematic Name | $^1$H-NMR (400 MHz, D$_6$-DMSO) | MS (Method) |
|---|---|---|---|
| | (1H-pyrrolo[2,3-b]pyridin-5-yl)-benzamide | 2H), 7.67 (m, 1H), 7.55 (d, 1H), 7.48 (m, 1H), 7.25 (m, 1H), 7.46 (m, 1H), 2.13 (s, 3H) | |
| 2-7 | 2-Chloro-5-(3-chloro-4-fluoro-benzoylamino)-N-(1H-pyrrolo[2,3-b]pyridin-5-yl)-benzamide | | |
| 2-8 | 1-(2-Methoxy-phenyl)-1H-pyrazole-3-carboxylic acid [4-chloro-3-(1H-pyrrolo[2,3-b]pyridin-5-ylcarbamoyl)-phenyl]-amide | | |

Example 3-1

2-Chloro-5-[4-(3,5-dimethyl-1H-pyrazol-4-yl)-benzoylamino]-N-(1H-pyrrolo[2,3-b]pyridin-5-yl)-benzamide 200 mg 4-(2-carboxyphenyl)-3,5-dimethylpyrazole (purchased from Fluorochem) were dissolved in 2 ml dry DMF. 225 mg N-methylmorpholine were added and the mixture was cooled to 0° C. 278 mg iso-butyl chloroformate were added slowly, and the mixture was allowed to reach room temperature. Stirring was continued for another 2 hrs, then the solvent was removed under vacuum to give 680 mg residue. 320 mg of this residue were dissolved in 1 ml dry DMF and added to a solution of 100 mg 1H-Pyrrolo[2,3-b]pyridin-5-ylamine in 1 ml dry DMF at RT. Stirring was continued over night before a few ml of water were added and the mixture was evaporated under vacuum. The residue was dissolved in 5 ml methanol and stirred with 1 ml conc. ammonia for 1 hr a RT to cleave any bis-acylated reaction products. It was again evaporated to dryness and the residue purified by chromatography on C-18 reversed phase silica in a water/methanol gradient. The first eluting product was 2-Chloro-5-[4-(3,5-dimethyl-1H-pyrazol-4-yl)-benzoylamino]-N-(1H-pyrrolo[2,3-b]pyridin-5-yl)-benzamide (3 mg), the second was [4-Chloro-3-(1H-pyrrolo[2,3-b]pyridin-5-ylcarbamoyl)-phenyl]-carbamic acid isobutyl ester (8 mg). $^1$H-NMR (400 MHz, D$_6$-DMSO); δ=12.14 (br, 1H), 11.60 (br, 1H), 10.52 (br, 1H), 10.24 (br, 1H), 8.39 (d, 1H), 8.35 (d, 1H), 7.84 (d, 1H), 7.69-7.50 (m, 2H), 7.57-7.43 (an, 4H), 7.27 (d, 1H), 6.45 (m, 1H), 2.07 (br, 3H), 2.01 (br, 3H)

MS (ESI-): m/z=483.40

Example 4-1

3-(2-Chloro-phenyl)-isoxazole-5-carboxylic acid [4-chloro-3-(1H-pyrrolo[2,3-b]pyridin-5-ylcarbamoyl)-phenyl]-amide 2-(1H-Benzotriazole-1-yl)-1,1,3,3-tetramethyluronium tetrafluoroborate (TBTU) (0.084 g, 0.26 mmol) and triethylamine (50 μL, 0.35 mmol) were added to a solution of 3-(2-chloro-phenyl)-2,3-dihydro-isoxazole-5-carboxylic acid (0.058 g, 0.26 mmol) in DMF (1 ml) and the reaction stirred for 10 minutes at room temperature. 5-Amino-2-chloro-N-(1H-pyrrolo[2,3-b]pyridin-5-yl)-benzamide (0.050 g, 0.175 mmol) was added to the reaction mixture and stirred for a further 24 hours. The solvent was removed under reduced pressure then methanol (3 ml) and ammonium hydroxide (1 ml) were added to the residue and the mixture stirred for a further 3 hours. The solvent was removed under reduced pressure and the resultant solid triturated with acetonitrile:water (1:1, 5 ml). The solid was filtered to afford 3-(2-Chloro-phenyl)-isoxazole-5-carboxylic acid [4-chloro-3-(1H-pyrrolo[2,3-b]pyridin-5-ylcarbamoyl)-phenyl]-amide 0.033 g (37% yield)

$^1$H-NMR (400 MHz, D$_6$-DMSO): δ=11.57 (br, 1H), 11.06 (br, 1H), 10.54 (br, 1H), 8.43 (d, 1H), 8.37 (m, 1H), 8.03 (d, 1H), 7.96 (m, 1H), 7.80 (m, 1H), 7.72 (s, 1H), 7.71 (m, 1H), 7.65-7.59 (m, 2H), 7.55 (m, 1H), 7.48 (m, 1H), 6.48 (m, 1H).

Examples 4-2 to 4-7

The following examples were, prepared analogously to the procedure described for Example 4-1, using the appropriate starting materials.

| Example No. | Systematic Name | $^1$H-NMR (400 MHz, D$_6$-DMSO) | MS (Method) |
|---|---|---|---|
| 4-2 | 5-Methyl-1-phenyl-1H-pyrazole-4-carboxylic acid [4-chloro-3-(1H-pyrrolo[2,3-b]pyridin-5-ylcarbamoyl)-phenyl]-amide | δ = 11.56 (br, 1H), 10.50 (s, 1H), 10.07 (s, 1H), 8.43 (m, 1H), 8.36 (m, 1H), 8.34 (s, 1H), 8.02 (m, 1H), 7.92 (m, 1H), 7.62-7.49 (m, 6H), 7.47 (m, 1H), 6.47 (m, 1H) | |
| 4-3 | 2-Chloro-5-(3-morpholin-4-yl-benzoylamino)-N-(1H- | δ = 11.57 (br, 1H), 10.51 (s, 1H), 10.38 (s, 1H), 8.42 (d, 1H), 8.36 (d, 1H), 8.03 (d, | |

| Example No. | Systematic Name | $^1$H-NMR (400 MHz, D$_6$-DMSO) | MS (Method) |
|---|---|---|---|
| | pyrrolo[2,3-b]pyridin-5-yl)-benzamide | 1H), 7.96 (m, 1H), 7.56 (d, 1H), 7.47 (m, 2H), 7.43-7.37 (m, 2H), 7.19 (m, 1H), 6.47 (m, 1H), 3.78 (t, 4H), 3.20 (t, 4H) | |
| 4-4 | 2-Chloro-5-[(E)-3-(2-methoxy-phenyl)-acryloylamino]-N-(1H-pyrrolo[2,3-b]pyridin-5-yl)-benzamide | δ = 11.57 (s, 1H), 10.51 (s, 1H), 10.45 (s, 1H), 8.42 (d, 1H), 8.36 (d, 1H), 7.96 (d, 1H), 7.87-7.81 (m, 2H), 7.60 (m, 1H), 7.54 (d, 1H), 7.48 (m, 1H), 7.42 (m, 1H), 7.12 (d, 1H), 7.03 (m, 1H), 6.88 (d, 1H), 6.47 (m, 1H), 3.91 (s, 3H) | |
| 4-5 | 5-(4-tert-Butoxy-benzoylamino)-2-chloro-N-(1H-pyrrolo[2,3-b]pyridin-5-yl)-benzamide | δ = 11.57 (br, 1H), 10.51 (s, 1H), 10.37 (s, 1H), 8.42 (d, 1H), 8.36 (d, 1H), 8.04 (d, 1H), 7.96-7.91 (m, 3H), 7.55 (d, 1H), 7.47 (m, 1H), 7.12 (m, 2H), 6.47 (m, 1H), 1.38 (s, 9H) | |
| 4-6 | 2-Chloro-5-[3-(cyano-dimethyl-methyl)-benzoylamino]-N-(1H-pyrrolo[2,3-b]pyridin-5-yl)-benzamide | δ = 11.57 (br, 1H), 10.54 (s, 1H), 10.52 (s, 1H), 8.43 (d, 1H), 8.37 (d, 1H), 8.07 (m, 1H), 8.02 (d, 1H), 7.99-7.95 (m, 2H), 7.78 (m, 1H), 7.65-7.57 (m, 2H), 7.47 (m, 1H), 6.47 (m, 1H), 1.76 (s, 6H) | |
| 4-7 | 2-Chloro-5-{[(1S,2S)-2-(4-methoxy-phenyl)-cyclopropanecarbonyl]-amino}-N-(1H-pyrrolo[2,3-b]pyridin-5-yl)-benzamide | δ = 11.56 (br, 1H), 10.49 (s, 1H), 10.46 (s, 1H), 8.40 (d, 1H), 8.34 (d, 1H), 7.88 (d, 1H), 7.69 (m, 1H), 7.49 (d, 1H), 7.47 (m, 1H), 7.12 (m, 2H), 6.87 (m, 2H), 6.46 (m, 1H), 3.73 (s, 3H), 2.36 (m, 1H), 2.00 (m, 1H), 1.47 (m, 1H), 1.33 (m, 1H) | |

Example 5-1

2-Chloro-5-((E)-3-pyrimidin-5-yl-acryloylamino)-N-(1H-pyrrolo[2,3-b]pyridin-5-yl)-benzamide TBTU (0.225 g, 0.70 mmol) and triethylamine (64 μL, 0.45 mmol) were added to a solution of (E)-3-pyrimidin-2-yl-acrylic acid (0.079 g, 0.53 mmol) in DMF (2 ml) and the reaction stirred for 10 minutes at room temperature. 5-Amino-2-chloro-N-(1H-pyrrolo[2,3-b]pyridin-5-yl)-benzamide (0.1 g, 0.35 mmol) was added to the reaction mixture and stirred at 70° C. for a further 24 hours. The solvent was removed under reduced pressure then methanol (5 ml) and ammonium hydroxide (2 ml) were added to the residue and the mixture stirred for a further 3 hours. The solvent was removed tinder reduced pressure and the solid triturated with acetonitrile; water (1:1, 5 ml). The solid was filtered to afford 3-(2-Chloro-phenyl)-isoxazole-5-carboxylic acid[4-chloro-3-(1H-pyrrolo[2,3-b]pyridin-5-ylcarbamoyl)-phenyl]-amide 0.065 g (44% yield)

Example 5-2

The following example was prepared analogously to the procedure described for Example 5-1, using the appropriate starting materials.

| Example No. | Systematic Name | $^1$H-NMR (400 MHz, D$_6$-DMSO) | MS (Method) |
|---|---|---|---|
| 5-2 | 2-Chloro-5-((E)-3-pyridazin-3-yl-acryloylamino)-N-(1H-pyrrolo[2,3-b]pyridin-5-yl)-benzamide | δ = 11.57 (br, 1H), 10.74 (s, 1H), 10.52 (s, 1H), 9.22 (m, 1H), 8.42 (d, 1H), 8.37 (d, 1H), 7.99 (d, 1H), 7.97 (m, 1H), 7.84 (m, 1H), 7.80-7.75 (m, 2H), 7.57 (d, 1H), 7.48 (m, 1H), 7.44 (d, 1H), 6.48 (m, 1H) | |

Example 6-1

5-benzoylamino-N-(3H-imidazo[4,5-b]pyridin-6-yl)-2-methyl-benzamide 50 mg of 5-Amino-N-(3H-imidazo[4,5-b]pyridin-6-yl)-2-methyl-benzamide (from example k) were dissolved in 0.5 ml dry DMF and 0.5 ml pyridine and treated dropwise at room temperature with 66 mg benzoyl chloride. After 16 hrs the solvents were removed under vacuum and the residue was stirred for 1 hr at room temperature in a mixture of 2 ml methanol and 1 ml concentrated ammonia. Solvents were removed under vacuum and the residue was purified by HPLC/MS in methanol/water/acetic acid. Product containing fractions were pooled and concentrated under vacuum. Precipitated product was collected by filtration and washed with dilute ammonia to yield 11 mg of the title product.

¹H-NMR (400 MHz, D₆-DMSO): δ-13.05 and 12.59 (s, 1H, tautomers), 10.62 and 10.51 (s, 1H, tautomers), 10.36 (s, 1H), 8.65-8.45 (m, 2H, tautomers), 8.41 (s, 1H), 8.03-7.92 (m, 3H), 7.85 (m, 1H), 7.64-7.51 (m, 3H), 7.32 (d, 1H), 2.39 (s, 3H)

MS (ESI+): m/z=372.3

Examples 6-2 to 6-4

The following examples were prepared analogously to the procedure described for Example 6-1, using the appropriate starting materials.

| Example No. | Systematic Name | ¹H-NMR (400 MHz, D₆-DMSO) | MS (Method) |
|---|---|---|---|
| 6-2 | Biphenyl-3-carboxylic acid [3-(3H-imidazo[4,5-b]pyridin-6-ylcarbamoyl)-4-methyl-phenyl]-amide | d = 10.60 (br, 1H), 10.45 (s, 1H), 8.60 (br, 1H), 8.56 (br, 1H), 8.47 (br, 1H), 8.25 (m, 1H), 7.97 (m, 2H), 7.89 (m, 2H), 7.78 (m, 2H), 7.65 (m, 1H), 7.53 (m, 2H), 7.43 (m, 1H), 7.34 (d, 1H), 2.40 (s, 3H) | 448.2 (ESI+) |
| 6-3 | Biphenyl-4-carboxylic acid [3-(3H-imidazo[4,5-b]pyridin-6-ylcarbamoyl)-4-methyl-phenyl]-amide | δ 13.21 (br, 1H), 11.01 (s, 1H), 10.83 (s, 1H), 9.00 (d, 2H), 8.84 (s, 1H), 8.51 (m, 2H), 8.42 (s, 1H), 8.35-8.23 (m, 3H), 8.19 (m, 2H), 7.94 (m, 2H), 7.86 (m, 1H), 7.75 (m, 1H), 2.82 (s, 3H) | 448.5 (ESI+) |
| 6-4 | N-(3H-Imidazo[4,5-b]pyridin-6-yl)-2-methyl-5-[(E)-3-phenyl-acryloyl)amino]-benzamide | d = 12.80 (br, 1H), 10.58 (s, 1H), 10.33 (s, 1H), 8.56 (m, 2H), 8.40 (s, 1H), 7.86 (s, 1H), 7.74 (m, 1H), 7.67-7.55 (m, 3H), 7.49-7.38 (m, 3H), 7.30 (d, 1H), 6.84 (d, 1H), 2.37 (s, 3H) | 398.2 (ESI+) |

Example 7-1

4-Chloro-N¹-(4-morpholin-4-yl-phenyl)-N³-(1H-pyrrolo[2,3-b]pyridin-5-yl)-isophthalamide 100 mg of 4-Chloro-N-(1H-pyrrolo[2,3-b]pyridin-5-yl)-isophthalamic in 1 ml dry DMF were treated with 56.5 mg carbonyldiimidazole and stirred for 1 hr at room temperature. 69 mg 4-morpholino-aniline and 10 mg 4-dimethylaminopyridine were added and the mixture was stirred 3 hrs at room temperature. The solvent was removed under vacuum and the residue dissolved in a mixture of 3 ml methanol and 0.5 ml concentrated ammonia. After stirring for 20 min at room temperature the solvents were removed and the residue purified by preparative HPLC/MS.

Yield 55 mg of the title product.

Example 8-1

4-Chloro-N¹-(6-phenoxy-pyridin-3-yl)-N³-(1H-pyrrolo[2,3-b]pyridin-5-yl)-isophthalamide hydrochloride Thionyl chloride (0.170 g, 1.43 mmol) and DMF (1 drop) were added to a solution of 4-Chloro-N-(1H-pyrrolo[2,3-b]pyridin-5-yl)-isophthalamic acid (0.15 g, 0.48 mmol) in THF (8 ml) and the reaction stirred at 50° C. for 16 hours. The reaction was concentrated under reduced pressure to give the crude acid chloride which was used without further purification.

6-Phenoxy-pyridin-3-ylamine (0.078 g, 0.42 mmol) was added to a solution of 4-chloro-3-(1H-pyrrolo[2,3-b]pyridin-5-ylcarbamoyl)-benzoyl chloride in DCM (5 ml) and the reaction stirred at room temperature for 2 hours. The solvent was removed under reduced pressure and the crude product triturated with acetonitrile:water (1:1, 10 ml). The solid was filtered to afford 4-Chloro-N¹-(6-phenoxy-pyridin-3-yl)-N³-(1H-pyrrolo[2,3-b]pyridin-5-yl)-isophthalamide as the hydrochloride salt, 0.086 g, (37% yield) over two steps.

Examples 8-2 to 8-8

The following examples were prepared analogously to the procedure described for Example 8-1, using the appropriate starting materials.

| Example No. | Systematic Name |
|---|---|
| 8-2 | 4-Chloro-N³-(1H-pyrrolo[2,3-b]pyridin-5-yl)-N¹-(4-trifluoromethyl-5,6,7,8-tetrahydro-quinazolin-2-yl)-isophthalamide hydrochloride |
| 8-3 | 4-Chloro-N¹-((1S,2R)-2-phenyl-cyclopropyl)-N³-(1H-pyrrolo[2,3-b]pyridin-5-yl)-isophthalamide hydrochloride |
| 8-4 | 4-Chloro-N¹-(3-morpholin-4-yl-phenyl)-N³-(1H-pyrrolo[2,3-b]pyridin-5-yl)-isophthalamide hydrochloride |
| 8-5 | 4-Chloro-N¹-(3-pyrazol-1-yl-phenyl)-N³-(1H-pyrrolo[2,3-b]pyridin-5-yl)-isophthalamide hydrochloride |
| 8-6 | 4-Chloro-N¹-(1-ethyl-3,3-dimethyl-2-oxo-2,3-dihydro-1H-indol-5-yl)-N³-(1H-pyrrolo[2,3-b]pyridin-5-yl)-isophthalamide hydrochloride |
| 8-7 | 4-Chloro-N¹-[3-(cyano-dimethyl-methyl)-phenyl]-N³-(1H-pyrrolo[2,3-b]pyridin-5-yl)-isophthalamide hydrochloride |
| 8-8 | 4-Chloro-N¹-(4-methyl-3-oxo-3,4-dihydro-2H-benzo[1,4]thiazin-7-yl)-N³-(1H-pyrrolo[2,3-b]pyridin-5-yl)-isophthalamide hydrochloride |
| 8-9 | 4-Chloro-N1-(4-methyl-3-oxo-3,4-dihydro-2H-benzo[1,4]oxazin-7-yl)-N3-(1H-pyrrolo[2,3-b]pyridin-5-yl)-isophthalamide |
| 8-10 | 4-Chloro-N1-[(1S,2R)-2-(2,5-dichloro-phenyl)-cyclopropyl]-N3-(1H-pyrrolo[2,3-b]pyridin-5-yl)-isophthalamide |
| 8-11 | 4-Chloro-N1-(4-methyl-3-oxo-3,4-dihydro-2H-benzo[1,4]oxazin-6-yl)-N3-(1H-pyrrolo[2,3-b]pyridin-5-yl)-isophthalamide |
| 8-12 | 4-Chloro-N1-(4-methyl-3-oxo-3,4-dihydro-2H-benzo[1,4]thiazin-7-yl)-N3-(1H-pyrrolo[2,3-b]pyridin-5-yl)-isophthalamide |

Examples 9-1 to 9-12

Example d-1

2-Methyl-5-nitro-N-(1H-pyrrolo[2,3-b]pyridin-5-yl)-benzamide

To a solution of 2-methyl-4-nitrobenzoic acid (2 g, 11 mmol) in benzene (40 ml) was added thionyl chloride (2 ml) and refluxed for 3 h. The reaction mixture was concentrated, diluted with dry acetonitrile (20 ml). To this solution was added dry $K_2CO_3$ (2 g, 14 mmol) followed by a solution of 1H-Pyrrolo[2,3-b]pyridin-5-ylamine (example c), 1.4 g, 11 mmol) in acetonitrile (20 ml) and the reaction mixture and stirred for 16 h at RT. Solvent was removed under reduced pressure, diluted with water stirred for 15 min and filtered. The solid residue was washed with EtOAc to get 2.4 g of crude title product. LC-MS: (m/z 297)

Example e-1

5-Amino-2-methyl-N-(1H-pyrrolo[2,3-b]pyridin-5-yl)-benzamide

To a solution of crude product from example d-1 (2.4 g) in methanol (50 ml) was added Zn dust (2 g) and aqueous solution of ammonium chloride (3 g) and the reaction mixture was refluxed for 1 h. The reaction mixture was cooled, filtered, concentrated under reduced pressure, diluted with water, stirred for 15 min, filtered and dried under high vacuum. The crude mass was stirred in aqueous ammonia for over night. The reaction mixture was concentrated under reduced pressure and washed with MeOH to get 1.3 g (46.4%, two steps) of the title product. $^1$H NMR (400 MHz, DMSO-$d_6$: 2.21 (s, 3H), 5.08 (bs, 2H), 6.42-6.43 (m, 1H), 6.57-6.59 (m, 1H), 6.69 (d, J=2 Hz, 1H), 6.92 (d, J=8.12 Hz, 1H), 7.43 (t, J=2.68 Hz, 1H), 8.36-8.42 (dd, J=1.88 Hz, 22.4 Hz, 2H), 10.18 (s, 1H), 11.56 (s, 1H).

General Preparation of Examples 9-1 to 9-12:
Examples 9-1 to 9-12 were Prepared by One of the Two Procedures Given Below:
(i) To a solution of 5-amino-2-methyl-N-(1H-pyrrolo[2,3-b]pyridin-5-yl)-benzamide (0.5 mmol) in $CH_3CN$ (5 ml) and $K_2CO_3$ (2 mmol) was added the appropriate acid chloride (0.5 mmol) [prepared from the acid and $SOCl_2$ in dry benzene under reflux for 3 h] and stirred at RT for overnight. Solvent was concentrated, washed with water and purified either by recrystallisation or by preparative HPLC to get pure 9-1 to 9-12.
(ii) To a solution of 5-Amino-2-methyl-N-(1H-pyrrolo[2,3-b]pyridin-5-yl)-benzamide (0.5 mmol) in DMF (5 ml) was added the appropriate acid (0.5 mmol), HBTU (0.5 mmol), HOBT (0.5 mmol) and Hunig's base (0.6 mmol) and stirred at RT for overnight. Solvent was concentrated, washed with water and purified either by silica gel column chromatography or by preparative HPLC to get pure 9-1 to 9-12.

The following examples were prepared analogously to the one of the two procedures described above, using the appropriate starting materials.

| Example No. | Systematic Name |
|---|---|
| 9-1 | 3,4,5-Trimethoxy-N-[4-methyl-3-(1H-pyrrolo[2,3-b]pyridin-5-ylcarbamoyl)-phenyl]-benzamide |
| 9-2 | 2,4,5-Trimethoxy-N-[4-methyl-3-(1H-pyrrolo[2,3-b]pyridin-5-ylcarbamoyl)-phenyl]-benzamide |
| 9-3 | 1-Phenyl-1H-pyrazole-4-carboxylic acid [4-methyl-3-(1H-pyrrolo[2,3-b]pyridin-5-ylcarbamoyl)-phenyl]-amide |
| 9-4 | 2-Methyl-5-(2-fluoro-5-trifluoromethyl-benzoylamino)-N-(1H-pyrrolo[2,3-b]pyridin-5-yl)-benzamide |
| 9-5 | 5-tert-Butyl-2-methyl-2H-pyrazole-3-carboxylic acid [4-methyl-3-(1H-pyrrolo[2,3-b]pyridin-5-ylcarbamoyl)-phenyl]-amide |
| 9-6 | 2-Methyl-5-(3-morpholin-4-yl-benzoylamino)-N-(1H-pyrrolo[2,3-b]pyridin-5-yl)-benzamide |
| 9-7 | 5-[(E)-3-(2-Methoxy-phenyl)-acryloylamino]-2-methyl-N-(1H-pyrrolo[2,3-b]pyridin-5-yl)-benzamide |
| 9-8 | 5-[(E)-3-(2,4-Dimethoxy-phenyl)-acryloylamino]-2-methyl-N-(1H-pyrrolo[2,3-b]pyridin-5-yl)-benzamide |
| 9-9 | 4-Methoxy-quinoline-2-carboxylic acid [4-methyl-3-(1H-pyrrolo[2,3-b]pyridin-5-ylcarbamoyl)-phenyl]-amide |
| 9-10 | 2-Methyl-5-(2-methoxy-5-trifluoromethoxy-benzoylamino)-N-(1H-pyrrolo[2,3-b]pyridin-5-yl)-benzamide |
| 9-11 | 3-(2-Chloro-phenyl)-isoxazole-5-carboxylic acid [4-methyl-3-(1H-pyrrolo[2,3-b]pyridin-5-ylcarbamoyl)-phenyl]-amide |
| 9-12 | 5-[(Z)-3-(2-Methoxy-phenyl)-acryloylamino] 2 methyl N (1H pyrrolo[2,3-b]pyridin 5 yl)-benzamide |

Examples 10-1 to 10-12

Example d-2

2-chloro-4-fluoro-5-nitrobenzoic acid

To a stirred solution of 2-chloro 4-fluoro-benzoic acid (50 g, 28.6 mmol) in conc. $H_2SO_4$ (259 ml) nitrating mixture (103 ml, conc. $H_2SO_4$-fuming $HNO_3$, 1:1) was added slowly from a dropping-funnel at 0° C. Reaction mass was stirred at 0° C. for 1 h. Same was warmed to RT stirred for 2 h. Reaction mass was poured into crushed ice. Solid was filtered and dried. Crude was purified by recrystatisation from EtOAc to get the title product as a white solid. $^1$H NMR (400 MHz, DMSO-$d_6$): δ 8.04 (d, 1H, J=11.08 Hz), 8.55 (d, J=8.16 Hz). FIA MS: (m/z 119).

Example d-3

2-Chloro-4-fluoro-5-nitro-N-(1H-pyrrolo[2,3-b]pyridin-5-yl)-benzamide

To a solution of 2-chloro-4-fluoro-5-nitrobenzoic acid from example d-2 (2 g, 9.1 mmol) in benzene (40 ml) was added thionyl chloride (2 ml) and refluxed for 3 h. The reaction mixture was concentrated, diluted with dry acetonitrile (20 ml). To this solution dry $K_2CO_3$, (2 g, 14 mmol) was added, followed by a solution of 1H-Pyrrolo[2,3-b]pyridin-5-ylamine (example c), 1.2 g, 9.1 mmol) in acetonitrile (20 ml) and the reaction mixture was stirred for 16 h at RT. Filtered the reaction mixture through cintered faunal. The residue was washed with dry acetonitrile several times. Solvent was removed under reduced pressure, 2.8 g of the crude title product. LC-MS: (m/z 335)

Example e-2

5-Amino-2-chloro-4-fluoro-N-(1H-pyrrolo[2,3-b]pyridin-5-yl)-benzamide

To a stirred solution of crude product from example d-3 (2.8 g) in EtOAc (50 ml), $SnCl_2$ (7.5 g) was added. The reaction mixture was stirred for 16 h. The reaction mixture was quenched with 1(N) NaOH and filtered through a pad of cilite. Organic layer was separated. Aqueous layer was extracted with EtOAc (3×50 ml). Organics was concentrated under reduced pressure and washed with Et$_2$O to get 1.1 g (40.4%, two steps) of the title product. $^1$H NMR (400 MHz, DMSO-d$_6$): δ 5.56 (bs, 2H), 6.43-6.44 (m, 1H), 6.94-6.96 (d, J=9.36 Hz, 1H), 7.27 (d, J=11.2 Hz, 1H), 7.45 (t, J=2.92 Hz, 1H), 8.33 (d, J=2.16 Hz, 1H), 8.38 (d, J=2.32 Hz, 1H), 10.39 (s, 1H), 11.60 (s, 1H).

General Preparation of Examples 10-1 to 10-10:

Examples 10-1 to 10-10 were Prepared by One of the Three Procedures Given Below:

i) To a solution of 5-ammo-2-chloro-4-fluoro-N-(1H-pyrrolo[2,3-b]pyridin-5-yl)-benzamide (0.5 mmol) in CH$_3$CN (5 ml), Cs$_2$CO$_3$ (2.5 mmol), and the appropriate acid chloride (0.5 mmol) [prepared from the acid and SOCl$_2$ in dry benzene under reflux for 3 h] were added and stirred at RT for overnight. Solvent was concentrated, diluted with EtOAc (10 ml) washed with water (2×5 ml). Organics was concentrated and crude was purified either by recrystallisation or by preparative HPLC to get pure 10-1 to 10-10.

ii) To a solution of 5-amino-2-chloro-4-fluoro-N-(1H-pyrrolo[2,3-b]pyridin-5-yl)-benzamide (0.5 mmol) in DMF (5 ml) were added the appropriate acid (0.5 mmol), HBTU (0.5 mmol), HOBT (0.5 mmol) and Hunig's base (0.6 mmol) and stirred at RT for overnight. Solvent was concentrated, diluted with EtOAc (10 ml) washed with water (2×5 ml). Organics was concentrated and crude was purified either by silica gel column chromatography or by preparative HPLC to get pure 10-1 to 10-10.

iii) To a suspension of NaH (0.5 mmol) in THF (3 ml), 5-amino-2-chloro-4-fluoro-N-(1H-pyrrolo[2,3-b]pyridin-5-yl)-benzamide (0.5 mmol) was added at 0° C. and stirred at RT for 1 h. The appropriate acid chloride dissolved in THF (2 ml) was added at 0° C. to the stirred solution of 9, warmed the reaction mixture to RT and stirred for over night. Reaction was quenched with NH$_4$Cl saturated solution. Reaction mass was diluted with 50 ml EtOAc and washed with water (2×25 ml). Organics was concentrated and crude was purified by preparative HPLC to get pure 10-1 to 10-10.

The following examples were prepared analogously to the one of the three procedures described above, using the appropriate starting materials.

| Example No. | Systematic Name |
|---|---|
| 10-1 | 2 Chloro-4-fluoro-5-(2-methoxy-5-trifluoromethoxy-benzoylamino)-N-(1H-pyrrolo[2,3-b]pyridin-5-yl)-benzamide |
| 10-2 | 1-Phenyl-1H-pyrazole-3-carboxylic acid [4-chloro-2-fluoro-5-(1H-pyrrolo[2,3-b]pyridin-5-ylcarbamoyl) phenyl]amide |
| 10-3 | 4-Methoxy-quinoline-2-carboxylic acid [4-chloro-2-fluoro-5-(1H-pyrrolo[2,3-b]pyridin-5-ylcarbamoyl)-phenyl]-amide |
| 10-4 | 5-tert-Butyl-2-methyl-2H-pyrazole-3-carboxylic acid [4-chloro-2-fluoro-5-(1H-pyrrolo[2,3-b]pyridin-5-ylcarbamoyl)-phenyl]-amide |
| 10-5 | 2-Chloro-4-fluoro-5-(3-morpholin-4-yl-benzoylamino)-N-(1H-pyrrolo[2,3-b]pyridin-5-yl)-benzamide |
| 10-6 | 2-Chloro-4-fluoro-5-(2-fluoro-4-trifluoromethyl-benzoylamino)-N-(1H-pyrrolo[2,3-b]pyridin-5-yl)-benzamide |
| 10-7 | 2-Chloro-4-fluoro-5 (2,4,5-trimethoxy-benzoylamino)-N-(1H-pyrrolo[2,3-b]pyridin-5-yl)-benzamide |
| 10-8 | 2-Chloro-4-fluoro-5-[(E)-3-(2-methoxy-phenyl)-acryloylamino]-N-(1H-pyrrolo[2,3-b]pyridin-5-yl)-benzamide |
| 10-9 | 2-Chloro-4-fluoro-5-(3,4,5-trimethoxy-benzoylamino)-N-(1H-pyrrolo[2,3-b]pyridin-5-yl)-benzamide |
| 10-10 | 3-(2-Chloro-phenyl)-isoxazole-5 carboxylic acid [4-chloro-2-fluoro-5-(1H-pyrrolo[2,3-b]pyridin-5-ylcarbamoyl)-phenyl]-amide |

Examples 11-1 to 11-9

Example 1-1

4-Methyl-isophthalic acid 1-tert-butyl ester

3-Amino-4-methylbenzoic acid was diazotized by stirring a solution in tetrafluoroboric acid at 0° C. NaNO2 was added slowly, stirred at same temperature for 1 h. White solid was filtered. Solid was washed with cooled water followed by Et2O. the crude diazonium salt was air dried and kept in freeze.

The above diazonium salt was carbonylated in MeOH solution. Argon was passed through the solution for 15 min. Pd(OAc)$_2$ was added into the reaction mixture under argon atmosphere at RT. Carbon monoxide was passed through the solution at RT under stirring for 1 h. Reaction mixture was filtered through celite bed. Organics was concentrated crude was purified by column chromatography to get 4-methyl-isophthalic acid 3-methyl ester. $^1$H NMR (400 MHz, DMSO-d$_6$): δ 2.58 (3H, s), 3.85 (3H, s), 7.47 (1H, d, J=7.97 Hz), 8.01 (1H, dd, J=1.64 Hz, J=7.88 Hz), 8.37 (1H, d, J=1.48 Hz), 13.19 (1H, bs). FIA MS: (m/z 194).

To a stirred solution of the above mono-ester in THF 4-DMAP was added slowly at 0° C. (BOC)$_2$O was added slowly to the reaction mixture and stirred for over night at RT. Reaction mass was concentrated and purified by column chromatography to get 4-Methyl-isophthalic acid 1 tert butyl ester 3-methyl ester. $^1$H NMR (400 MHz, DMSO-d$_6$): δ 1.57 (9H, s), 2.50 (3H, s), 3.85 (3H, s), 7.46 (1H, d, J=8.04 Hz), 7.96 (1H, dd, J=1.84 Hz, J=7.96 Hz), 8.30 (1H, d, J=1.8 Hz). FIA MS: (m/z 250)

To a stirred solution of the above mixed methyl-(tert.-butyl) ester in DMF-H2O, NaOH was added. Reaction mixture was stirred at RT for over night. After completion of the reaction pH of the reaction mass was adjusted by using 1 (N) HCl to neutral. Reaction mass was extracted by EtOAc. Organics was concentrated; residue was purified by column chromatography to get 4-methyl-isophthalic acid 1-tert-butyl ester as white solid. $^1$H NMR (400 MHz, DMSO-d$_6$): δ 1.54 (9H, s), 2.53 (3H, s), 7.43 (1H, d, J=8 Hz), 7.93 (1H, dd, J=1.68 Hz, J=7.96 Hz), 8.31 (1H, d, J=1.44 Hz), 13.15 (1H, bs). FIA MS: (m/z 236).

Example m-1

4-Methyl-N-(1H-pyrrolo[2,3-b]pyridin-5yl)-isophthalamic acid tert-butyl ester ii) To a solution of 1H-pyrrolo[2,3-b]pyridin-5-ylamine (example c), 0.5 mmol) and 4-methyl-isophthalic acid 1-tert-butyl ester from example 1-1 (0.5 mmol) in THF (5 ml) were added TBTU (0.5 mmol), HOBT (0.5 mmol) and Hunig's base (0.6 mmol) and stirred at RT for overnight. Solvent was concentrated, residue was diluted with EtOAc ( ), washed with 1(N) NaOH. Organics was concentrated to get 2.8 g of the crude title product. LC-MS: (m/z 352)

Example n-1

4-Methyl-N-(1H-pyrrolo[2,3-b]pyridin-5-yl)-isophthalamic acid

A solution of crude product from example m-1) (2.8 g) in TFA (5 ml) was stirred for 2 h at RT. TFA was removed completely to get the title product. LC-MS (m/z 296)
General Preparation of Examples 11-1 to 11-9:
Examples 11-1 to 11-9 were Prepared by the Procedure Given Below:

To a solution of 4-methyl-N-(1H-pyrrolo[2,3-b]pyridin-5-yl)-isophthalamic acid (0.5 mmol) in DMF (5 ml) were added the appropriate amine (0.5 mmol), HBTU (0.5 mmol), HOBT (0.5 mmol) and Hunig's base (0.6 mmol) and stirred at RT for overnight. Solvent was concentrated, washed with water and purified either by silica gel column chromatography or by preparative HPLC to get pure 11-1 to 11-9.

The following examples were prepared analogously to the procedure described above, using the appropriate starting materials.

| Example No. | Systematic Name |
|---|---|
| 11-1 | 4-Methyl-N3-(1H-pyrrolo[2,3-b]pyridin-5-yl)-N1-(6-trifluoromethyl-pyridin-3-yl)-isophthalamide |
| 11-2 | N1-(2-Methoxy-5-trifluoromethyl-phenyl)-4-methyl-N3-(1H-pyrrolo[2,3-b]pyridin-5-yl)-isophthalamide |
| 11-3 | 4-Methyl-N1-(2-phenyl-cyclopropyl)-N3-(1H-pyrrolo[2,3-b]pyridin-5-yl)-isophthalamide |
| 11-4 | 4-Methyl-N1-(3-oxazol-5-yl-phenyl)-N3-(1H-pyrrolo[2,3-b]pyridin-5-yl)-isophthalamide |
| 11-5 | N1-(3-Methoxy-5-trifluoromethyl-phenyl)-4-methyl-N3-(1H-pyrrolo[2,3-b]pyridin-5-yl)-isophthalamide |
| 11-6 | 4-Methyl-N3-(1H-pyrrolo[2,3-b]pyridin-5-yl)-N1-(3,4,5-trimethoxy-phenyl)-isophthalamide |
| 11-7 | N1-(5-tert-Butyl-2-methyl-2H-pyrazol-3-yl)-4-methyl-N3-(1H-pyrrolo[2,3-b]pyridin-5-yl)-isophthalamide |
| 11-8 | 4-Methyl-N1-(3-morpholin-4-yl-phenyl)-N3-(1H-pyrrolo[2,3-b]pyridin-5-yl)-isophthalamide |
| 11-9 | 4-Methyl-N1-(3-pyrazol-1-yl-phenyl)-N3-(1H-pyrrolo[2,3-b]pyridin-5-yl)-isophthalamide |

Example 12

2-Chloro-5-[4-(2-hydroxyethyl)amino-3-chloro-benzoylamino]-N-(1H-1-pyrrolo[2,3-b]pyridin-5-yl)-benzamide 50 mg of 2-chloro-5-[3-chloro-4-fluoro-benzoylamino]-N-(1H-pyrrolo[2,3-b]pyridin-5-yl)-benzamide from example 2-7 and 1 g of 2-aminoethanol were heated to 140° C. for 1 hr. The mixture was concentrated under high vacuum, the residue was taken up in a small amount of methanol and the crude product precipitated by addition of water. Chromatography on silica in ethyl acetate yielded 18.9 mg of the title product.

The invention claimed is:
1. A compound according to formula I, formula I

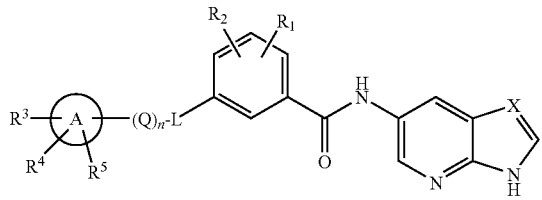

wherein,
$R^1$ and $R^2$ are each independently selected from the group consisting of: hydrogen, halogen, alkyl, alkoxy, trifluoromethyl, trifluoromethoxy, difluoromethyl, and difluoromethoxy;
L is —NH—C(O)— or —C(O)—NH—;
Q is selected from the group consisting of: alkylene, alkenylene, and cycloalkylene;
n is 0 or 1;
ring A is aryl or heteroaryl
$R^3$ is selected from the group consisting of:
  a) hydrogen;
  b) —V-phenyl, which is optionally substituted by fluorine, chlorine, bromine, alkyl, alkoxy, trifluoromethyl, trifluoromethoxy, cyano or —Y-alkylene-Z;
  c) heteroaryl, which is optionally substituted by fluorine, chlorine, alkyl, alkoxy, oxo, trifluoromethyl or trifluoromethoxy;
  d) -T-heterocyclyl, which is optionally substituted by alkyl, —C(O)-alkyl, or —S(O)$_2$-alkyl; and
  e) alkoxy;
$R^4$ is selected from the group consisting of: hydrogen, halogen, alkyl, alkoxy, trifluoromethyl, trifluoromethoxy, cyano, and —Y-alkylene-Z;
$R^5$ is selected from the group consisting of: hydrogen, alkyl, fluorine, chlorine, alkoxy, and cyano;
V is a single bond or —O—;
T is a single bond or alkylene;
X is N or CH;
Y is selected from the group consisting of: a single bond, —O—, —NR—, —S—, and —S(O)$_2$—;
Z is selected from the group consisting of: —OR, —NRR', —C(O)—NRR', cyano, —NRR'-C(O)-alkyl, —S(O)$_2$-alkyl, —S(O)$_2$—NRR', and —NR—S(O)$_2$-alkyl; and
R and R' are each independently hydrogen or alkyl;
or a pharmaceutically acceptable salt thereof.
2. A compound according to claim 1, wherein
$R^1$ and $R^2$ are each independently selected from the group consisting of: hydrogen, chlorine, fluorine, and methyl;
Q is alkenylene or cycloalkylene;
n is 0 or 1;
ring A is phenyl or a heteroaryl selected from the group consisting of pyrazolyl, isoxazolyl, quinolyl, pyridyl, pyridazinyl, pyrimidyl, 3-oxo-3,4-dihydro-2H-benzo[1,4]oxazin-6-yl, 3,4-dihydro-2H-benzo[1,4]oxazin-7-yl, 5,6,7,8-tetrahydro-quinazolin-2-yl, 2,3-dihydro-1H-indol-5-yl, and 3,4-dihydro-2H-benzo[1,4]thiazin-7-yl;
$R^3$ is selected from the group consisting of:
  a) hydrogen;
  b) —V-phenyl, which is optionally substituted once or twice by chlorine, alkoxy, or —Y-alkylene-Z;
  c) pyrazolyl which is optionally substituted once or twice by alkyl;
  d) oxazolyl which is optionally substituted once or twice by alkyl;
  e) -T-morpholinyl; and
  f) alkoxy;
$R^4$ is selected from the group consisting of: hydrogen, chlorine, alkyl, alkoxy, trifluoromethyl, trifluoromethoxy, and —Y-alkylene-Z;
$R^5$ is selected from the group consisting of: hydrogen, alkyl, fluorine, chlorine, alkoxy, and cyano;
T is a single bond;
X is N or CH;
Y is selected from the group consisting of: a single bond, —O—, —NR—, and —S—;

Z is selected from the group consisting of: —OR, —NRR', —C(O)—NRR', and cyano; and R and R' are each independently hydrogen or alkyl.

3. A compound according to claim 1, wherein L is —C(O)—NH—.

4. A compound according to claim 1, wherein L is —NH—C(O)—.

5. A compound according to claim 1, wherein X is CH.

6. A compound according to claim 1, wherein X is N.

7. A compound according claim 1 selected from the group consisting of:

3'-(2-Dimethylamino-ethoxy)-biphenyl-4-carboxylic acid [4-chloro-3-(1H-pyrrolo[2,3-b]pyridin-5-ylcarbamoyl)-phenyl]-amide;

3'-(1-Carbamoyl-ethylsulfanyl)-biphenyl-4-carboxylic acid [4-chloro-3-(1H-pyrrolo[2,3-b]pyridin-5-ylcarbamoyl)-phenyl]-amide;

Biphenyl-3-carboxylic acid [4-chloro-3-(1H-pyrrolo[2,3-b]pyridin-5-ylcarbamoyl)-phenyl]-amide;

Biphenyl-4-carboxylic acid [4-chloro-3-(1H-pyrrolo[2,3-b]pyridin-5-ylcarbamoyl)-phenyl]-amide;

2-Chloro-5-(4-morpholin-4-yl-benzoylamino)-N-(1H-pyrrolo[2,3-b]pyridin-5-yl)-benzamide;

2-Chloro-5-[4-(3,5-dimethyl-1H-pyrazol-4-yl)-benzoylamino]-N-(1H-pyrrolo[2,3-b]pyridin-5-yl)-benzamide;

2-Chloro-5-(3-morpholin-4-yl-benzoylamino)-N-(1H-pyrrolo[2,3-b]pyridin-5-yl)-benzamide;

5-(4-tert-Butoxy-benzoylamino)-2-chloro-N-(1H-pyrrolo[2,3-b]pyridin-5-yl)-benzamide;

2-Chloro-5-[3-(cyano-dimethyl-methyl)-benzoylamino]-N-(1H-pyrrolo[2,3-b]pyridin-5-yl)-benzamide;

3-(2-Chloro-phenyl)-isoxazole-5-carboxylic acid [4-chloro-3-(1H-pyrrolo[2,3-b]pyridin-5-ylcarbamoyl)-phenyl]-amide;

5-Methyl-1-phenyl-1H-pyrazole-4-carboxylic acid [4-chloro-3-(1H-pyrrolo[2,3-b]pyridin-5-ylcarbamoyl)-phenyl]-amide;

2-Chloro-5-((E)-3-phenyl-but-2-enoylamino)-N-(1H-pyrrolo[2,3-b]pyridin-5-yl)-benzamide;

2-Chloro-5-{3-[4-(3-dimethylamino-propoxy)-phenyl]-acryloylamino}-N-(1H-pyrrolo[2,3-b]pyridin-5-yl)-benzamide;

2-Chloro-5-[3-(3-cyano-phenyl)-2-methyl-acryloylamino]-N-(1H-pyrrolo[2,3-b]pyridin-5-yl)-benzamide;

2-Chloro-5-[(E)-3-(2-methoxy-phenyl)-acryloylamino]-N-(1H-pyrrolo[2,3-b]pyridin-5-yl)-benzamide; and 2-Chloro-5-{[(1S,2S)-2-(4-methoxy-phenyl)-cyclopropanecarbonyl]-amino}-N-(1H-pyrrolo[2,3-b]pyridin-5-yl)-benzamide;

2-Chloro-5-((E)-3-pyrimidin-5-yl-acryloylamino)-N-(1H-pyrrolo[2,3-b]pyridin-5-yl)-benzamide;

2-Chloro-5-((E)-3-pyridazin-3-yl-acryloylamino)-N-(1H-pyrrolo[2,3-b]pyridin-5-yl)-benzamide;

5-Benzoylamino-N-(3H-imidazo[4,5-b]pyridin-6-yl)-2-methyl-benzamide;

Biphenyl-3-carboxylic acid [3-(3H-imidazo[4,5-b]pyridin-6-ylcarbamoyl)-4-methyl-phenyl]-amide;

Biphenyl-4-carboxylic acid [3-(3H-imidazo[4,5-b]pyridin-6-ylcarbamoyl)-4-methyl-phenyl]-amide;

N-(3H-Imidazo[4,5-b]pyridin-6-yl)-2-methyl-5-[(E)-(3-phenyl-acryloyl)amino]-benzamide;

4-Chloro-$N^1$-(4-morpholin-4-yl-phenyl)-$N^3$-(1H-pyrrolo[2,3-b]pyridin-5-yl)-isophthalamide;

4-Chloro-$N^1$-(3-morpholin-4-yl-phenyl)-$N^3$-(1H-pyrrolo[2,3-b]pyridin-5-yl)-isophthalamide hydrochloride;

4-Chloro-$N^1$-(3-pyrazol-1-yl-phenyl)-$N^3$-(1H-pyrrolo[2,3-b]pyridin-5-yl)-isophthalamide hydrochloride;

4-Chloro-$N^1$-[3-(cyano-dimethyl-methyl)-phenyl]-$N^3$-(1H-pyrrolo[2,3-b]pyridin-5-yl)-isophthalamide hydrochloride;

4-Chloro-$N^3$-(1H-pyrrolo[2,3-b]pyridin-5-yl)-$N^1$-(4-trifluoromethyl-5,6,7,8-tetrahydro-quinazolin-2-yl)-isophthalamide hydrochloride;

4-Chloro-$N^1$-(6-phenoxy-pyridin-3-yl)-$N^3$-(1H-pyrrolo[2,3-b]pyridin-5-yl)-isophthalamide hydrochloride;

4-Chloro-$N^1$-(1-ethyl-3,3-dimethyl-2-oxo-2,3-dihydro-1H-indol-5-yl)-$N^3$-(1H-pyrrolo[2,3-b]pyridin-5-yl)-isophthalamide hydrochloride;

4-Chloro-$N^1$-(4-methyl-3-oxo-3,4-dihydro-2H-benzo[1,4]thiazin-7-yl)-$N^3$-(1H-pyrrolo[2,3-b]pyridin-5-yl)-isophthalamide hydrochloride;

4-Chloro-$N^1$-((1S,2R)-2-phenyl-cyclopropyl)-$N^3$-(1H-pyrrolo[2,3-b]pyridin-5-yl)-isophthalamide; hydrochloride;

2-Chloro-5-(3-chloro-4-fluoro-benzoylamino)-N-(1H-pyrrolo[2,3-b]pyridin-5-yl)-benzamide;

1-(2-Methoxy-phenyl)-1H-pyrazole-3-carboxylic acid [4-chloro-3-(1H-pyrrolo[2,3-b]pyridin-5-ylcarbamoyl)-phenyl]-amide;

3,4,5-Trimethoxy-N-[4-methyl-3-(1H-pyrrolo[2,3-b]pyridin-5-ylcarbamoyl)-phenyl]-benzamide;

2,4,5-Trimethoxy-N-[4-methyl-3-(1H-pyrrolo[2,3-b]pyridin-5-ylcarbamoyl)-phenyl]-benzamide;

1-Phenyl-1H-pyrazole-4-carboxylic acid [4-methyl-3-(1H-pyrrolo[2,3-b]pyridin-5-ylcarbamoyl)-phenyl]-amide;

2-Methyl-5-(2-fluoro-5-trifluoromethyl-benzoylamino)-N-(1H-pyrrolo[2,3-b]pyridin-5-yl)-benzamide;

5-tert-Butyl-2-methyl-2H-pyrazole-3-carboxylic acid [4-methyl-3-(1H-pyrrolo[2,3-b]pyridin-5-ylcarbamoyl)-phenyl]-amide;

2-Methyl-5-(3-morpholin-4-yl-benzoylamino)-N-(1H-pyrrolo[2,3-b]pyridin-5-yl)-benzamide;

5-[(E)-3-(2-Methoxy-phenyl)-acryloylamino]-2-methyl-N-(1H-pyrrolo[2,3-b]pyridin-5-yl)-benzamide;

5-[(E)-3-(2,4-Dimethoxy-phenyl)-acryloylamino]-2-methyl-N-(1H-pyrrolo[2,3-b]pyridin-5-yl)-benzamide;

4-Methoxy-quinoline-2-carboxylic acid [4-methyl-3-(1H-pyrrolo[2,3-b]pyridin-5-ylcarbamoyl)-phenyl]-amide;

2-Methyl-5-(2-methoxy-5-trifluoromethoxy-benzoylamino)-N-(1H-pyrrolo[2,3-b]pyridin-5-yl)-benzamide;

3-(2-Chloro-phenyl)-isoxazole-5-carboxylic acid [4-methyl-3-(1H-pyrrolo[2,3-b]pyridin-5-ylcarbamoyl)-phenyl]-amide;

5-[(Z)-3-(2-Methoxy-phenyl)-acryloylamino]-2-methyl-N-(1H-pyrrolo[2,3-b]pyridin-5-yl)-benzamide;

2-Chloro-4-fluoro-5-(2-methoxy-5-trifluoromethoxy-benzoylamino)-N-(1H-pyrrolo[2,3-b]pyridin-5-yl)-benzamide;

1-Phenyl-1H-pyrazole-3-carboxylic acid [4-chloro-2-fluoro-5-(1H-pyrrolo[2,3-b]pyridin-5-ylcarbamoyl)-phenyl]-amide;

4-Methoxy-quinoline-2-carboxylic acid [4-chloro-2-fluoro-5-(1H-pyrrolo[2,3-b]pyridin-5-ylcarbamoyl)-phenyl]-amide;

5-tert-Butyl-2-methyl-2H-pyrazole-3-carboxylic acid [4-chloro-2-fluoro-5-(1H-pyrrolo[2,3-b]pyridin-5-yl-carbamoyl)-phenyl]-amide;

2-Chloro-4-fluoro-5-(3-morpholin-4-yl-benzoylamino)-N-(1H-pyrrolo[2,3-b]pyridin-5-yl)-benzamide;

2-Chloro-4-fluoro-5-(2-fluoro-4-trifluoromethyl-benzoylamino)-N-(1H-pyrrolo[2,3-b]pyridin-5-yl)-benzamide;

2-Chloro-4-fluoro-5-(2,4,5-trimethoxy-benzoylamino)-N-(1H-pyrrolo[2,3-b]pyridin-5-yl)-benzamide;

2-Chloro-4-fluoro-5-[(E)-3-(2-methoxy-phenyl)-acryloylamino]-N-(1H-pyrrolo[2,3-b]pyridin-5-yl)-benzamide;

2-Chloro-4-fluoro-5-(3,4,5-trimethoxy-benzoylamino)-N-(1H-pyrrolo[2,3-b]pyridin-5-yl)-benzamide;

3-(2-Chloro-phenyl)-isoxazole-5-carboxylic acid [4-chloro-2-fluoro-5-(1H-pyrrolo[2,3-b]pyridin-5-yl-carbamoyl)-phenyl]-amide;

4-Methyl-$N^3$-(1H-pyrrolo[2,3-b]pyridin-5-yl)-$N^1$-(6-trifluoromethyl-pyridin-3-yl)-isophthalamide;

$N^1$-(2-Methoxy-5-trifluoromethyl-phenyl)-4-methyl-$N^3$-(1H-pyrrolo[2,3-b]pyridin-5-yl)-isophthalamide;

4-Methyl-$N^1$-(2-phenyl-cyclopropyl)-$N^3$-(1H-pyrrolo[2,3-b]pyridin-5-yl)-isophthalamide;

4-Methyl-$N^1$-(3-oxazol-5-yl-phenyl)-$N^3$-(1H-pyrrolo[2,3-b]pyridin-5-yl)-isophthalamide;

$N^1$-(3-Methoxy-5-trifluoromethyl-phenyl)-4-methyl-$N^3$-(1H-pyrrolo[2,3-b]pyridin-5-yl)-isophthalamide;

4-Methyl-$N^3$-(1H-pyrrolo[2,3-b]pyridin-5-yl)-$N^1$-(3,4,5-trimethoxy-phenyl)-isophthalamide;

$N^1$-(5-tert-Butyl-2-methyl-2H-pyrazol-3-yl)-4-methyl-$N^3$-(1H-pyrrolo[2,3-b]pyridin-5-yl)-isophthalamide;

4-Methyl-$N^1$-(3-morpholin-4-yl-phenyl)-$N^3$-(1H-pyrrolo[2,3-b]pyridin-5-yl)-isophthalamide;

4-Methyl-$N^1$-(3-pyrazol-1-yl-phenyl)-$N^3$-(1H-pyrrolo[2,3-b]pyridin-5-yl)-isophthalamide; and 2-Chloro-5-[4-(2-hydroxyethyl)amino-3-chloro-benzoylamino]-N-(1H-pyrrolo[2,3-b]pyridin-5-yl)-benzamide.

8. A process for the preparation of a compound according to claim 1, comprising reacting a compound of formula XIIIa,

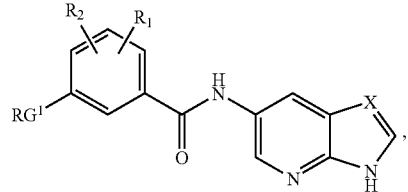

formula XIIIa wherein $R^1$, $R^2$ and X have the meaning as defined for formula I in claim 1, and $RG^1$ is either —$NH_2$ or —C(O)OH, with a compound of formula XIVa,

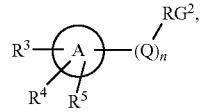

formula XIVa wherein ring A, $R^3$, $R^4$, $R^5$, Q and n have the meaning as defined for formula I in claim 1, and $RG^2$ is either —C(O)OH, if $RG^1$ is —$NH_2$; or $RG^2$ is —$NH_2$, if and $RG^1$ is —C(O)OH, to give the compounds of formula I,

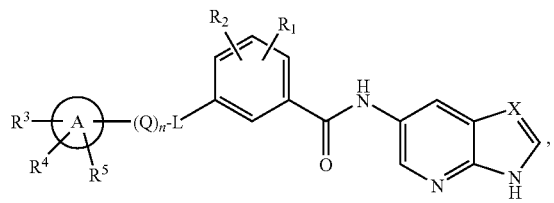

formula I wherein ring A, $R^1$, $R^2$, $R^3$, $R^4$, $R^5$, Q, n, X and L have the meaning as defined for formula I in claim 1.

9. A pharmaceutical composition, containing a compound according to claim 1 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 8,067,599 B2 | Page 1 of 1 |
| APPLICATION NO. | : 12/374682 | |
| DATED | : November 29, 2011 | |
| INVENTOR(S) | : Honold et al. | |

It is certified that error appears in the above-identified patent and that said Letters Patent is hereby corrected as shown below:

TITLE PAGE,
Item (73) Assignee: "Hoffman-La Roche Inc., Nutley, NJ (US)" should read
--Hoffmann-La Roche Inc., Nutley, NJ (US)--.

Signed and Sealed this
Twenty-first Day of February, 2012

David J. Kappos
*Director of the United States Patent and Trademark Office*